United States Patent [19]

Girodeau

[11] Patent Number: 5,132,328
[45] Date of Patent: Jul. 21, 1992

[54] ALCOHOL AND ETHER DERIVATIVES

[75] Inventor: Jean-Marc M. M. Girodeau, Rilly la Montagne, France

[73] Assignees: Imperial Chemical Industries PLC, London, England; ICI Pharma, Reims Cedex, France

[21] Appl. No.: 454,919

[22] Filed: Dec. 22, 1989

[30] Foreign Application Priority Data

Dec. 23, 1988 [EP] European Pat. Off. ........ 88403312.7

[51] Int. Cl.$^5$ .................. A61K 31/085; C07C 43/20; C07C 43/215; C07C 43/205
[52] U.S. Cl. .................... 514/716; 514/719; 514/720; 514/721; 568/586; 568/609; 568/633; 568/644; 568/645; 568/646
[58] Field of Search ............. 568/586, 609, 633, 644, 568/645, 646; 514/716, 719, 720, 721

[56] References Cited

U.S. PATENT DOCUMENTS

| | | | |
|---|---|---|---|
| 4,876,346 | 10/1989 | Musser | 546/172 |
| 4,918,081 | 4/1990 | Huang et al. | 514/311 |
| 4,920,130 | 4/1990 | Huang | 514/311 |
| 4,920,131 | 4/1990 | Huang | 514/311 |
| 4,920,132 | 4/1990 | Huang | 514/314 |
| 4,920,133 | 4/1990 | Huang | 514/314 |

FOREIGN PATENT DOCUMENTS

| | | |
|---|---|---|
| 0349062 | 7/1980 | European Pat. Off. |
| 0110405 | 6/1984 | European Pat. Off. |
| 0181568 | 5/1986 | European Pat. Off. |
| 0190722 | 8/1986 | European Pat. Off. |
| 0200101 | 12/1986 | European Pat. Off. |
| 0271287 | 6/1988 | European Pat. Off. |

*Primary Examiner*—Mary E. Ceperley

*Attorney, Agent, or Firm*—Cushman, Darby & Cushman

[57] ABSTRACT

The invention concerns a compound of the formula I,

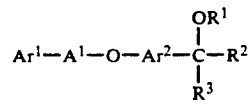

wherein $Ar^1$ is optionally substituted phenyl or naphthyl;

$A^1$ is (1-6C)alkylene, (3-6C)alkenylene, (3-6C)alkynylene or cyclo(3-6C)alkylene;

$Ar^2$ is optionally substituted phenylene, or a 6 membered heterocyclene moiety containing up to three nitrogen atoms;

$R^1$ is hydrogen, (1-6C)alkyl, (3-6C)alkenyl, (3-6C)alkynyl, cyano-(1-4C)alkyl or (2-4C)alkanoyl, or optionally substituted benzoyl;

wherein $R^2$ is hydrogen, (1-6C)alkyl, (2-6C)alkenyl, (2-6C)alkynyl or substituted (1-4C)alkyl; and wherein $R^3$ is hydroxy-(1-4C)alkyl, mercapto-(1-4C)alkyl, (1-4C)alkoxy-(1-4C)alkyl, (3-4C)alkenyloxy-(1-4C)alkyl, (3-4C)alkynyloxy-(1-4C)alkyl, (1-4C)alkoxy-(2-4C)alkoxy-(1-4C)alkyl, (1-4C)alkylthio-(1-4C)alkyl, (1-4C)alkylsulphinyl-(1-4C)alkyl, (1-4C)alkylsulphonyl-(1-4C)alkyl, (1-4C)alkoxycarbonyl-(1-4C)alkyl, (2-4C)alkanoyl-(1-4C)alkyl, (2-4C)alkanoyloxy-(1-4C)alkyl or cyano-(1-4C)alkyl; or $R^3$ is oxiranyl, oxetanyl, tetrahydrofuranyl or tetrahydropyranyl;

or a pharmaceutically-acceptable salt thereof.

The compounds of the invention are inhibitors of the enzyme 5-lipoxygenase.

9 Claims, No Drawings

ALCOHOL AND ETHER DERIVATIVES

This invention concerns novel alcohol and ether derivatives and more particularly novel alcohol and ether derivatives which are inhibitors of the enzyme 5-lipoxygenase (hereinafter referred to as 5-LO). The invention also concerns processes for the manufacture of said derivatives and novel pharmaceutical compositions containing said derivatives. Also included in the invention is the use of said derivatives in the treatment of various inflammatory and/or allergic diseases in which the direct or indirect products of 5-LO catalysed oxidation of arachidonic acid are involved, and the production of new medicaments for such use.

As stated above the alcohol and ether derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain alcohol and ether derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a compound of the formula I (set out hereinafter) wherein $Ar^1$ is phenyl or naphthyl which may optionally bear one or more substituents selected from halogeno, hydroxy, carboxy, cyano, (1–4C)alkyl, (2–4C)alkenyl, (2–4C)alkynyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–4C)alkyl and fluoro-(1–4C)alkyl;

wherein $A^1$ is (1–6C)alkylene, (3–6C)alkenylene, (3–6C)alkynylene or cyclo(3–6C)alkylene;

wherein $Ar^2$ is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkylsulphonyl, (1–4C)alkylamino, di-[(1–4C)alkyl]amino, fluoro-(1–4C)alkyl, (1–4C)alkoxycarbonyl, N-[(1–4C)alkyl]carbamoyl, N,N-di[(1–4C)alkyl]carbamoyl, (2–4C)alkanoylamino, cyano-(1–4C)alkoxy, carbamoyl-(1–4C)alkoxy and (1–4C)alkoxycarbonyl-(1–4C)alkoxy;

$Ar^2$ is a 6-membered heterocyclene moiety containing up to three nitrogen atoms;

wherein $R^1$ is hydrogen, (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ is hydrogen, (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl or (2–4C)alkanoyloxy-(1–4C)alkyl;

wherein $R^3$ is hydroxy-(1–4C)alkyl, mercapto-(1–4C)alkyl, (1–4C)alkoxy-(1–4C)alkyl, (3–4C)alkenyloxy-(1–4C)alkyl, (3–4C)alkynyloxy-(1–4C)alkyl, (1–4C)alkoxy-(2–4C)alkoxy-(1–4C)alkyl, (1–4C)alkylthio-(1–4C)alkyl, (1–4C)alkylsulphinyl-(1–4C)alkyl, (1–4C)alkylsulphonyl-(1–4C)alkyl, (1–4C)alkoxycarbonyl-(1–4C)alkyl, (2–4C)alkanoyl-(1–4C)alkyl, (2–4C)alkanoyloxy-(1–4C)alkyl or cyano-(1–4C)alkyl; or $R^3$ is oxiranyl, oxetanyl, tetrahydrofuranyl or tetrahydropyranyl;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for a halogeno substituent which may be present on $Ar^1$, $Ar^2$ or $R^1$ is, for example, fluoro, chloro, bromo or iodo.

A suitable value for a (1–4C)alkyl substituent which may be present on $Ar^1$, $Ar^2$ or $R^1$ is, for example, methyl, ethyl, propyl, isopropyl, butyl, isobutyl, sec-butyl or tert-butyl.

A suitable value for a (2–4C)alkenyl substituent on $Ar^1$ is, for example, vinyl, allyl, 2-butenyl or 3-butenyl.

A suitable value for a (2–4C)alkynyl substituent on $Ar^1$ is, for example, ethynyl, 1-propynyl, 2-propynyl, 1-butynyl or 2-butynyl.

A suitable value for a (1–4C)alkoxy substituent which may be present on $Ar^1$, $Ar^2$ or $R^1$ is, for example, methoxy, ethoxy, propoxy, isopropoxy or butoxy.

A suitable value for a (2–4C)alkanoyl substituent which may be present on $Ar^1$ or for $R^1$ when it is (2–4C)alkanoyl is, for example, acetyl, propionyl or butyryl.

Suitable values for substituents which may be present on Ar¹ or Ar² include, for example:

| | |
|---|---|
| for (1–4C)alkythio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for (1–4C)alkylamino: | methylamino, ethylamino propylamino and butylamino; |
| for di-[(1–4C)alkyl]amino: | dimethylamino, diethylamino and dipropylamino; |
| for (1–4C)alkoxycarbonyl: | methoxycarbonyl, ethoxycarbonyl and tert-butoxycarbonyl; |
| for fluoro-(1–4C)alkyl: | fluoromethyl, difluoromethyl, trifluoromethyl, 2-fluoroethyl, 2,2,2-trifluoroethyl and pentafluoroethyl. |

A suitable value for a hydroxy-(1–4C)alkyl substituent which may be present on Ar¹ is, for example, hydroxymethyl, 1-hydroxyethyl, 2-hydroxyethyl, 1-hydroxypropyl, 2-hydroxypropyl or 3-hydroxypropyl.

A suitable value for the number of substituents which may be present on Ar¹ is, for example, one, two or three.

A suitable value for A¹ when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for A¹ when it is cyclo(3–6C)alkylene is, for example, cyclopropylidene, 1,2-cyclopropylene, cyclopentylidene, 1,2-cyclopentylene, cyclohexylidene or 1,4-cyclohexylene.

A suitable value for Ar² when it is phenylene is, for example, 1,3-phenylene or 1,4-phenylene.

A suitable value for Ar² when it is a 6-membered heterocyclene moiety containing up to three nitrogen atoms is, for example, pyridylene, pyrimidinylene, pyridazinylene, pyrazinylene or 1,3,5-triazinylene. Conveniently Ar² when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on Ar² include, for example:

| | |
|---|---|
| for (3–4C)alkenyloxy: | allyloxy, methylallyoxy, but-2-enyloxy and but-3-enyloxy; |
| for N-[(1–4C)alkyl]carbamoyl: | N-methylcarbamoyl, N-ethylcarbamoyl and N-propylcarbamoyl; |
| for N,N-di-[(1–4C)alkyl]carbamoyl: | N,N-dimethylcarbamoyl and N,N-diethylcarbamoyl; |
| for (2–4C)alkanoylamino: | acetamido, propionamido and butyramido; |
| for cyano-(1–4C)alkoxy: | cyanomethoxy, 2-cyanoethoxy and 3-cyanopropoxy; |
| for carbamoyl-(1–4C)alkoxy: | carbamoylmethoxy, 2-carbamoylethoxy and 3-carbamoylpropoxy; |
| for (1–4C)alkoxycarbonyl-(1–4C)-alkoxy: | methoxycarbonylmethoxy, 2-methoxycarbonylethoxy, ethoxycarbonylmethoxy and 2-ethoxycarbonylethoxy. |

A suitable value for R¹ or R² when it is (1–6C)alkyl is, for example, methyl, ethyl, propyl, butyl, pentyl or hexyl.

A suitable value for R¹ when it is (3–6C)alkenyl is, for example, allyl, 2-butenyl or 3-butenyl; and when it is (3–6C)alkynyl is, for example, 2-propynyl or 2-butynyl.

A suitable value for R² when it is (2–6C)alkenyl is, for example, vinyl, allyl, 2-butenyl or 3-butenyl; and when it is (2–6C)alkynyl is, for example, ethynyl, 1-propynyl, 2-propynyl, 1-butynyl or 2-butynyl.

A suitable value for R¹, R² or R³ when it is cyano-(1–4C)alkyl is, for example, cyanomethyl, 2-cyanoethyl or 3-cyanopropyl.

A suitable value for R² when it is fluoro-(1–4C)alkyl is, for example, fluoromethyl, difluoromethyl, trifluoromethyl, 2-fluoroethyl, 2,2,2-trifluoroethyl or pentafluoroethyl.

A suitable value for R² or R³ when it is hydroxy-(1–4C)alkyl is, for example, hydroxymethyl, 1-hydroxyethyl, 2-hydroxyethyl, 1-hydroxypropyl, 2-hydroxypropyl or 3-hydroxypropyl; when it is (1–4C)alkoxy-(1–4C)alkyl is, for example, methoxymethyl, 1-methoxyethyl, 2-methoxyethyl, 1-methoxypropyl, 2-methoxypropyl, 3-methoxypropyl, ethyoxymethyl, 1-ethoxyethyl, 2-ethoxyethyl, 1-ethoxypropyl, 2-ethoxypropyl or 3-ethoxypropyl; and when it is (2–4C)alkanoyloxy-(1–4C)alkyl is, for example, acetoxymethyl, 2-acetoxyethyl, 3-acetoxypropyl, propionyloxymethyl, 2-propionyloxyethyl or 3-propionyloxypropyl.

A suitable value for R³ when it is mercapto-(1–4C)alkyl is, for example, mercaptomethyl, 1-mercaptoethyl, 2-mercaptoethyl, 1-mercaptopropyl, 2-mercaptopropyl or 3-mercaptopropyl; when it is (3–4C)alkenyloxy-(1–4C)alkyl is, for example, allyloxymethyl, 1-(allyloxy)ethyl or 2-(allyloxy)ethyl; when it is (3–4C)alkynyloxy-(1–4C)alkyl is, for example, 2-propynyloxymethyl, 1-(2-propynyloxy)ethyl or 2-(2-propynyloxy)ethyl; when it is (1–4C)alkoxy-(2–4C)alkoxy-(1–4C)alkyl is, for example, 2-methoxyethoxymethyl or 2-ethoxyethoxymethyl; when it is (1–4C)alkylthio-(1–4C)alkyl is, for example, methylthiomethyl, 1-methylthioethyl, 2-methylthioethyl, 1-methylthiopropyl, 2-methylthiopropyl, 3-methylthiopropyl, ethylthiomethyl, 1-ethylthioethyl, 2-ethylthioethyl, 1-ethylthiopropyl, 2-ethylthiopropyl or 3-ethylthiopropyl; when it is (1–4C)alkylsulphinyl-(1–4C)alkyl is, for example, methylsulphinylmethyl, 1-methylsulphinylethyl, 2-methylsulphinylethyl, 1-methylsulphinylpropyl, 2-methylsulphinylpropyl or 3-methylsulphinylpropyl; when it is (1–4C)alkylsulphonyl-(1–4C)alkyl is, for example, methylsulphonylmethyl, 1-methylsulphonylethyl, 2-methylsulphonylethyl, 1-methylsulphonylpropyl, 2-methylsulphonylpropyl or 3-methylsulphonylpropyl; when it is (1–4C)alkoxycarbonyl-(1–4C)alkyl is, for example, methoxycarbonylmethyl, 2-methoxycarbonylethyl, ethoxycarbonylmethyl or 2-ethoxycarbonylethyl; and when it is (2–4C)alkanoyl-(1–4C)alkyl is, for example, acetonyl, 2-oxobutyl, 3-oxobutyl, 3-oxopentyl or 4-oxopentyl.

A suitable value for R³ when it is oxetanyl, tetrahydrofuranyl or tetrahydropyranyl is, for example, 2-oxetanyl, 3-oxetanyl, 2-tetrahydrofuranyl, 3-tetrahydrofuranyl, 2-tetrahydropyranyl, 3-tetrahydropyranyl or 4-tetrahydropyranyl.

A suitable pharmaceutically-acceptable salt of a compound of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic (for example a compound of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example compounds of the formula I wherein:

(a) $Ar^1$ is phenyl, naphth-1-yl or naphth-2-yl which may optionally bear one, two or three substituents selected from fluoro, chloro, bromo, iodo, cyano, methyl, methoxy, methylthio, methylsulphinyl, methylsulphonyl, methoxycarbonyl, difluoromethyl and trifluoromethyl; and $A^1$, $Ar^2$, $R^1$, $R^2$ and $R^3$ have any of the meanings defined hereinbefore;

(b) $Ar^1$ is phenyl or naphth-2-yl which may optionally bear one or two substituents selected from fluoro, chloro, bromo, methyl, tert-butyl and trifluoromethyl; and $A^1$, $Ar^2$, $R^1$, $R^2$ and $R^3$ have any of the meanings defined hereinbefore;

(c) $A^1$ is methylene, ethylene, trimethylene, 1-propenylene, 2-methylprop-1-enylene or 1-propynylene and $Ar^1$, $Ar^2$, $R^1$, $R^2$ and $R^3$ have any of the meanings defined hereinbefore;

(d) $A^1$ is methylene, 1-propenylene or 1-propynylene; and $Ar^1$, $Ar^2$, $R^1$, $R^2$ and $R^3$ have any of the meanings defined hereinbefore;

(e) $Ar^2$ is 1,3-phenylene or 1,4-phenylene which may optionally bear one substituent selected from chloro, bromo, hydroxy, amino, nitro, methyl, methoxy, allyloxy, methylthio, methylsulphinyl, methylsulphonyl, methylamino, dimethylamino, trifluoromethyl, acetamido, cyanomethoxy and carbamoylmethoxy and $Ar^1$, $A^1$, X, $R^1$, $R^2$ and $R^3$ have any of the meanings defined hereinbefore;

(f) $Ar^2$ is 1,3-phenylene or 1,4-phenylene which may optionally bear one substituent selected from fluoro, chloro, methoxy and trifluoromethyl; and $Ar^1$, $A^1$, $R^1$, $R^2$ and $R^3$ have any of the meanings defined hereinbefore;

(g) $Ar^2$ is 2,4-, 2,5-, 3,5- or 2,6-pyridylene or 4,6-pyrimidylene; and $Ar^1$, $A^1$, $R^1$, $R^2$ and $R^3$ have any of the meanings defined hereinbefore;

(h) $Ar^2$ is 3,5-pyridylene; and $Ar^1$, $A^1$, $R^1$, $R^2$ and $R^3$ have any of the meanings defined hereinbefore;

(i) $R^1$ is hydrogen, methyl, ethyl, allyl, 2-propynyl or cyanomethyl; and $Ar^1$, $A^1$, $Ar^2$, $R^2$ and $R^3$ have any of the meanings defined hereinbefore;

(j) $R^1$ is methyl, ethyl or allyl; and $Ar^1$, $A^1$, $Ar^2$, $R^2$ and $R^3$ have any of the meanings defined hereinbefore;

(k) $R^2$ is hydrogen, methyl, ethyl, propyl, vinyl, ethynyl, 1-propynyl, trifluoromethyl, hydroxymethyl, methoxymethyl or acetoxymethyl; and $Ar^1$, $A^1$, $Ar^2$, $R^1$ and $R^3$ have any of the meanings defined hereinbefore;

(l) $R^2$ is methyl, ethyl, hydroxymethyl or methoxymethyl; and $Ar^1$, $A^1$, $Ar^2$, $R^1$ and $R^3$ have any of the meanings defined hereinbefore;

(m) $R^3$ is hydroxymethyl, 1-hydroxyethyl, 2-hydroxyethyl, mercaptomethyl, 1-mercaptoethyl, 2-mercaptoethyl, methoxymethyl, 1-methoxyethyl, 2-methoxyethyl, ethoxymethyl, methylthiomethyl, 1-methylthioethyl, 2-methylthioethyl, methylsulphonylmethyl, methoxycarbonylmethyl, ethoxycarbonylmethyl, acetoxymethyl or cyanomethyl; and $Ar^1$, $A^1$, $Ar^2$, $R^1$ and $R^2$ have any of the meanings defined hereinbefore;

(n) $R^3$ is hydroxymethyl, 1-hydroxyethyl, 2-hydroxyethyl, mercaptomethyl, methoxymethyl, 1-methoxyethyl, 2-methoxyethyl, ethoxymethyl, allyloxymethyl, 2-propynyloxymethyl, 1-(2-propynyloxy)ethyl, 2-methoxyethoxymethyl, methylthiomethyl, 1-methylthioethyl, 2-methylthioethyl, methoxycarbonylmethyl, ethoxycarbonylmethyl, 2-acetylethyl, acetoxymethyl or cyanomethyl; and $Ar^1$, $A^1$, $Ar^2$, $R^1$ and $R^2$ have any of the meanings defined hereinbefore;

(o) $R^3$ is oxiranyl, 2-oxetanyl, 2-tetrahydrofuranyl or 2-tetrahydropyranyl; and $Ar^1$, $A^1$, $Ar^2$, $R^1$ and $R^2$ have any of the meanings defined hereinbefore;

or a pharmaceutically-acceptable salt thereof.

A preferred compound of the invention comprises a compound of the formula I wherein $Ar^1$ is phenyl or naphth-2-yl which may optionally bear one substituent selected from fluoro, methyl and trifluoromethyl;

$A^1$ is methylene, 1-propenylene or 1-propynylene;

$Ar^2$ is 1,3-phenylene or 1,4-phenylene which may optionally bear one substituent selected from fluoro, methoxy and trifluoromethyl; or $Ar^2$ is 3,5-pyridylene;

$R^1$ is methyl or ethyl;

$R^2$ is methyl, ethyl, hydroxymethyl or methoxymethyl; and $R^3$ is 1-hydroxyethyl, 2-hydroxyethyl, mercaptomethyl, methoxymethyl, 1-methoxyethyl, 2-methoxyethyl, ethoxymethyl, 2-propynyloxymethyl, 1-(2-propynyloxy)ethyl, methylthiomethyl, 1-methylthioethyl, 2-methylthioethyl, acetoxymethyl or cyanomethyl;

or a pharmaceutically-acceptable salt thereof.

A further preferred compound of the invention comprises a compound of the formula I wherein $Ar^1$ is naphth-2-yl or 7-fluoronaphth-2-yl;

$A^1$ is methylene;

$Ar^2$ is 1,3-phenylene or 5-fluoro-1,3-phenylene;

$R^1$ is methyl;

$R^2$ is methyl, ethyl or methoxymethyl; and $R^3$ is mercaptomethyl, methoxymethyl, 1-methoxyethyl or 2-propynyloxymethyl;

or a pharmaceutically-acceptable salt thereof.

A further preferred compound of the invention comprises a compound of the formula I wherein $Ar^1$ is phenyl; $A^1$ is 1-propynylene; $Ar^2$ is 1,3-phenylene or 5-fluoro-1,3-phenylene; $R^1$ is methyl; $R^2$ is methyl or ethyl; and $R^3$ is methoxymethyl;

or pharmaceutically-acceptable salts thereof.

Specific especially preferred compounds of the invention include, for example, the following compounds of the formula I, or pharmaceutically-acceptable salts thereof:

2-methoxy-2-[3-(naphth-2-ylmethoxy)phenyl]but-1-yl methyl ether, 2-methoxy-2-[3-(naphth-2-ylmethoxy)phenyl]prop-1-yl methyl ether, 2-methoxy-2-[3-(naphth-2-ylmethoxy)phenyl]but-3-yl methyl sulphide,
2-methoxy-2-[3-(naphth-2-ylmethoxy)phenyl]but-1-yl 2-propynyl ether,
2-[5-fluoro-3-(7-fluoronaphth-2-ylmethoxy)phenyl]-2-methoxybut-1-yl methyl ether and
2-methoxy-2-[5-fluoro-3-(3-phenylprop-2-ynyloxy)-phenyl]but-1-yl methyl ether.

A compound of the invention comprising an alcohol or ether derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $A^1$, $Ar^2$, $R^1$, $R^2$ and $R^3$ have any of the meanings defined hereinbefore.

(a) The alkylation, in the presence of a suitable base, of a compound of the formula II with a compound of the formula $Ar^1$-$A^1$-Z wherein Z is a displaceable group; provided that, when there is an amino, alkylamino, hydroxy or carboxy group in $Ar^1$, $Ar^2$, $R^1$, $R^2$ or $R^3$, any amino, alkylamino or carboxy group is protected by a conventional protecting group and any hydroxy group may be protected by a conventional protecting group or alternatively any hydroxy group need not be protected; whereafter any undesired protecting group in $Ar^1$, $Ar^2$, $R^1$, $R^2$ or $R^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

A suitable protecting group for an amino or alkylamino group is, for example, an acyl group for example a (1-4C)alkanoyl group (especially acetyl), a (1-4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1-4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting material of the formula II may be obtained by standard procedures of organic chemistry. The preparation of examples of such starting materials is described within the accompanying non-limiting Examples which are provided for the purposes of illustration only. Thus the starting material of the formula II may be obtained, for example, by deprotecting a protected ether derivative of the formula III wherein $R^4$ is a protecting group and $Ar^2$, $R^1$, $R^2$ and $R^3$ have the meanings defined hereinbefore.

A suitable protecting group $R^4$ is, for example, an arylmethyl group (especially benzyl), a tri-(1-4C)alkylsilyl group (especially trimethylsilyl or t-butyldimethylsilyl), an aryldi-(1-4C)alkylsilyl group (especially dimethylphenylsilyl), a (1-4C)alkyl group (especially methyl), a (1-4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryl dialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide. Alternatively a (1-4C)alkoxymethyl group or a tetrahydropyranyl group may be removed, for example, by treatment with a suitable acid such as hydrochloric or trifluoroacetic acid.

The protecting group $R^4$ may be, for example, a tri-(1-4C)alkylsilyl group which can be removed while the protecting group for any amino, imino, alkylamino, carboxy or hydroxy group in $Ar^2$, $R^1$, $R^2$ or $R^3$ is retained.

The protected starting material of the formula III may be obtained by standard procedures of organic chemistry. Thus, for example, an alcohol of the formula $R^4$—O—$Ar^2$—CH(OH)—$R^3$, wherein $R^4$ is a protecting group as defined hereinbefore, may be obtained by the reaction of an aldehyde of the formula $R^4$—O—$Ar^2$—CHO with an organometallic compound of the formula $R^3$—M or $R^3$—M—Z, wherein $R^3$ has the meaning defined hereinbefore, M is a metallic group, for example lithium, magnesium or zinc, and Z is a halogeno group, for example chloro, bromo or iodo, and provided that any amino, alkylamino, or hydroxy group in $Ar^2$ or $R^3$ is protected by a conventional protecting group. The reaction may be carried out in, for example, a suitable solvent or diluent such as an ether (for example tetrahydrofuran, t-butylmethylether or diethyl ether) at a temperature in the range, for example, −100° to 50° C. (especially −80° to 30° C.).

The secondary alcohol of the formula $R^4$—O—$Ar^2$—CH(OH)—$R^3$ may be oxidised to give a ketone of the formula $R^4$—O—$Ar^2$—CO—$R^3$. A particular suitable oxidising agent is, for example, any agent known in the art for the oxidation of a secondary alcohol to a ketone, for example, manganese dioxide, chromium trioxide pyridine complex, 2,3-dichloro-5,6-dicyano-1,4-benzoquinone (hereinafter DDQ), a mixture of dimethylsulphoxide, oxalyl chloride and triethylamine, a mixture of acetic anhydride and dimethylsulphoxide or a mixture of dimethylsulphoxide and a dialkylcarbodiimide, for example, N,N'-dicyclohexylcarbodiimide or N-ethyl-N'-(3-dimethylaminopropyl)carbodiimide.

A tertiary alcohol of the formula IV, wherein $R^4$ has the meaning defined hereinbefore, may be obtained by the reaction of the ketone $R^4$—O—$Ar^2$—CO—$R^3$ with an organometallic compound of the formula $R^2$—M—Z, wherein M is a metallic group, for example magnesium, and Z is a halogeno group, for example chloro, bromo or iodo, and provided that any amino, alkylamino or hydroxy group in $Ar^2$, $R^2$ or $R^3$ is protected by a conventional protecting group. The reaction may be carried out in a suitable solvent or diluent such as an ether (for example tetrahydrofuran, t-butyl methyl ether or diethyl ether) at a temperature in the range, for example, −30° to 100° C. (especially ambient temperature to 80° C.).

It will be appreciated that the tertiary alcohol of the formula IV may be obtained from the aldehyde of the formula $R^4$—O—$Ar^2$—CHO by reversing the order of introduction of the groups $R^3$ and $R^2$. Thus the aldehyde of the formula $R^4$—O—$Ar^2$—CHO may be treated initially with the organometallic compound of the formula $R^2$—M—Z, the product so obtained may be oxidised using a suitable oxidising agent as described above and the resultant ketone may be treated with the organometallic compound $R^3$—M or $R^3$—M—Z to give the compound of the formula IV, and provided that any amino, alkylamino or hydroxy group in $Ar^2$, $R^2$ or $R^3$ is protected by a conventional protecting group.

The protected ether derivative of the formula III, wherein $R^4$ has the meaning defined hereinbefore, may be obtained by the alkylation of the tertiary alcohol of the formula IV with an alkylating agent of the formula $R^1$—Z, wherein Z is a displaceable group as defined hereinbefore, in the presence of a suitable base as defined hereinbefore, and provided that any amino, alkylamino or hydroxy group in $Ar^2$, $R^2$ or $R^3$ is protected by a conventional protecting group;

Alternatively the tertiary alcohol starting material of the formula IV may be obtained by the reaction of a compound of the formula $R^4$—O—$Ar^2$—Z, wherein $R^4$ and $Ar^2$ have the meanings defined hereinbefore and Z is a halogeno group as defined hereinbefore and provided that any amino, alkylamino or hydroxy group in $Ar^2$ is protected with a conventional protecting group, with either an organometallic compound of the formula $R^6$—M, wherein $R^6$ is a (1-6C)alkyl group such as butyl and M is a metallic group, for example lithium, to give an organometallic compound of the formula $R^4$—O—$Ar^2$—M, or with a metal such as magnesium to given an organometallic compound of the formula $R^4$—O—$Ar^2$—M—Z; whereaftereither of these organometallic compounds may be reacted with a ketone of the formula $R^2$—CO—$R^3$, wherein $R^2$ and $R^3$ have the meanings defined hereinbefore, and provided that any hydroxy group in $R^2$ and $R^3$ is protected by a conventional protecting group.

(b) The alkylation, in the presence of a suitable base as defined hereinbefore, of a compound of the formula V with a compound of the formula $R^1$—Z, wherein $R^1$ and Z have the meanings defined hereinbefore, provided that, when there is an amino, alkylamino, hydroxy or carboxy group in $Ar^1$, $Ar^2$, $R^2$ or $R^3$, any amino, alkylamino, hydroxy or carboxy group is protected by a conventional protecting group; whereafter any undesired protecting group in $Ar^1$, $Ar^2$, $R^2$ or $R^3$ is removed by conventional means.

The tertiary alcohol starting material of the formula V may be obtained, for example, by the reaction of an aldehyde of the formula $Ar^1$—$A^1$—O—$Ar^2$—CHO with an organometallic compound of the formula $R^3$—M or $R^3$—M—Z, having the meaning defined hereinbefore and using the conditions defined hereinbefore, to give a secondary alcohol of the formula $Ar^1$—$A^1$—O—$Ar^2$—CH(OH)—$R^3$ and provided that any amino, alkylamino, carboxy or hydroxy group in $Ar^1$, $Ar^2$ or $R^3$ is protected by a conventional protecting group. The product so obtained may be oxidised using a suitable oxidising agent, as defined hereinbefore, to give a ketone of the formula $Ar^1$—$A^1$—O—$Ar^2$—CO—$R^3$, which in turn may be treated with an organometallic compound of the formula $R^2$—M—Z, having the meaning defined hereinbefore and using the conditions defined hereinbefore, to give the required tertiary alcohol starting material of the formula V.

It will be appreciated that the tertiary alcohol of the formula V may be obtained from the aldehyde of the formula $Ar^1$—$A^1$—O—$Ar^2$—CHO by reversing the order of the introduction of the groups $R^3$ and $R^2$, i.e. by reaction of the aldehyde of the formula $Ar^1$—$A^1$—O—$Ar^2$—CHO with the organometallic compound of the formula $R^2$—M—Z, oxidation of the secondary alcohol to a ketone of the formula $Ar^1$—$A^1$—O—$Ar^2$—CO—$R^2$ and reaction of said ketone with the organometallic compound of the formula $R^3$—M or $R^3$—M—Z, and provided that any amino, alkylamino, carboxy or hydroxy group in $Ar^1$, $Ar^2$, $R^2$ or $R^3$ is protected by a conventional protecting group.

Alternatively the ketone intermediate of the formula $Ar^1$—$A^1$—O—$Ar^2$—CO—$R^2$ may be obtained, for example, by the alkylation, in the presence of a suitable base as defined hereinbefore, of a ketone of the formula H—O—$Ar^2$—CO—$R^2$ with a compound of the formula $Ar^1$—$A^1$—Z, wherein Z is a displaceable group as defined hereinbefore, and provided that any amino, alkylamino, carboxy or hydroxy group in $Ar^1$ or $Ar^2$ is protected by a conventional protecting group.

The aldehyde starting material of the formula $Ar^1$—$A^1$—O—$Ar^2$—CHO may be obtained, for example, by the alkylation, in the presence of a suitable base as defined hereinbefore, of an aldehyde of the formula H—O—Ar$^2$—CHO with a compound of the formula Ar$^1$—A$^1$—Z, wherein Z is a displaceable group, as defined hereinbefore, and provided that any amino, alkylamino, carboxy or hydroxy group in Ar$^1$ or Ar$^2$ is protected by a conventional protecting group.

Alternatively the tertiary alcohol starting material of the formula V may be obtained, for example, by the reaction of an ester of the formula Ar$^1$—A$^1$—O—Ar$^2$—CO$_2$R$^5$, wherein R$^5$ is a (1-4C)alkyl group such as methyl or ethyl, with an organometallic compound of the formula R$^3$—M or R$^3$—M—Z, having the meaning defined hereinbefore and using the conditions defined hereinbefore for the corresponding reaction of the aldehyde of the formula R$^4$—O—Ar$^2$—CHO, and provided that any amino, alkylamino, carboxy or hydroxy group in Ar$^1$, Ar$^2$ or R$^3$ is protected by a conventional protecting group, to give a ketone of the formula Ar$^1$—A$^1$—O—Ar$^2$—CO—R$^3$. The product so obtained may be treated with an organometallic compound of the formula R$^2$—M—Z, having the meaning defined hereinbefore and using the conditions defined hereinbefore, to give the required tertiary alcohol starting material of the formula V.

It will be appreciated that the tertiary alcohol of the formula V may be obtained from the ester of the formula Ar$^1$—A$^1$—O—Ar$^2$—CO$_2$R$^5$ by reversing the order of the introduction of the groups R$^3$ and R$^2$, i.e. by reaction of the ester of the formula Ar$^1$—A$^1$—O—Ar$^2$—CO$_2$R$^5$ with the organometallic compound of the formula R$^2$—M—Z, to give a ketone of the formula Ar$^1$—A$^1$—O—Ar$^2$—CO—R$^2$ and reaction of said ketone with the organometallic compound of the formula R$^3$—M or R$^3$—M—Z and provided that any amino, alkylamino, carboxy or hydroxy group in Ar$^1$, Ar$^2$, R$^2$ or R$^3$ is protected by a conventional protecting group.

The ester starting material of the formula Ar$^1$—A$^1$—O—Ar$^2$—CO$_2$R$^5$ may be obtained, for example, by the alkylation, in the presence of a suitable base as defined hereinbefore, of an ester of the formula H—O—Ar$^2$—CO$_2$R$^5$, wherein R$^5$ has the meaning defined hereinbefore, with a compound of the formula Ar$^1$—A$^1$—Z, wherein Z is a displaceable group as defined hereinbefore, and provided that any amino, alkylamino, carboxy or hydroxy group in Ar$^1$ or Ar$^2$ is protected by a conventional protecting group.

Alternatively the ketone of the formula Ar$^1$—A$^1$—O—Ar$^2$—CO—R$^3$ may be obtained by the reaction of a nitrile of the formula Ar$^1$—A$^1$—O—Ar$^2$—CN with an organometallic compound of the formula R$^3$—M or R$^3$—M—Z using the conditions defined hereinbefore for the corresponding reaction of the aldehyde of the formula R$^4$—O—Ar$^2$—CHO.

Alternatively the tertiary alcohol starting material of the formula V may be obtained, for example, by the alkylation, in the presence of a suitable base, of a compound of the formula HO—Ar$^2$—Z, wherein Ar$^2$ has the meaning defined hereinbefore and Z is a halogeno group as defined hereinbefore, with a compound of the formula Ar$^1$—A$^1$—Z, wherein Ar$^1$, A$^1$ and Z have the meanings defined hereinbefore, and provided that any amino, alkylamino, carboxy or hydroxy group in Ar$^1$ or Ar$^2$ is protected by a conventional protecting group, to give a compound of the formula Ar$^1$—A$^1$—O—Ar$^2$—Z. The product so obtained may be treated either with an organometallic compound of the formula R$^6$—M, wherein R$^6$ is a (1-6C)alkyl group such as butyl and M is a metallic group, for example lithium, to give an organometallic compound of the formula Ar$^1$—A$^1$—O—Ar$^2$—M, or with a metal such as magnesium to give an organometallic compound of the formula Ar$^1$—A$^1$—O—Ar$^2$—M—Z. Either of these organometallic compounds may be reacted with a ketone of the formula R$^2$—CO—R$^3$, provided that any hydroxy group in R$^2$ or R$^3$ is protected by a conventional protecting group, to give the required tertiary alcohol starting material of the formula V.

(c) For the production of those compounds of the formula I wherein Ar$^1$ or Ar$^2$ bears an alkylsulphinyl or alkylsulphonyl substituent, or R$^3$ is an alkylsulphinylalkyl or alkylsulphonylalkyl group, the oxidation of a compound of the formula I wherein Ar$^1$ or Ar$^2$ bears an alkylthio substituent or wherein R$^3$ is an alkylthioalkyl group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(d) For the production of those compounds of the formula I wherein Ar$^2$ bears an alkanoylamino substituent, the acylation of a compound of the formula I wherein Ar$^2$ bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(e) For the production of those compounds of the formula I wherein R$^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent as defined hereinbefore. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore.

(f) For the production of those compounds of the formula I wherein $Ar^1$ bears an alkenyl substituent, $A^1$ is alkenylene, or $R^1$ or $R^2$ is alkenyl, the reduction of the corresponding compound wherein $Ar^1$ bears an alkynyl substituent, $A^1$ is alkynylene, $R^1$ is alkynyl or $R^2$ is alkynyl. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1-6C)alkylaluminium hydride such as diisobutylaluminium hydride, and an alkyl metal, for example a (1-6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C.).

(g) For the production of those compounds of the formula I wherein $Ar^2$ or $R^3$ bears an alkoxy or substituted alkoxy substituent, an alkenyloxy substituent or an alkynyloxy substituent, the alkylation of a compound of the formula I wherein $Ar^2$ or $R^3$ bears a hydroxy substituent.

A suitable alkylating agent is, for example any agent known in the art for the alkylation of hydroxy to alkoxy or substituted alkoxy, or alkenyloxy or alkynyloxy, for example an alkyl or substituted alkyl halide, for example a (1-6C)alkyl chloride, bromide or iodide or a substituted (1-4C)alkyl chloride, bromide or iodide, in the presence of a suitable base, or for example an alkenyl or alkynyl halide, for example a (3-4C)alkenyl chloride or bromide or a (3-4C)alkynyl chloride or bromide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III, IV and V and these are provided as a further feature of the invention.

As stated previously, the alcohol and ether derivatives of the formula I are inhibitors of the enzyme 5-LO. The effects of this inhibition may be demonstrated using one or more of the standard procedures set out below:

(a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

(b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

(c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

(d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

(e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in vivo model for 5-LO inhibitors administered topically or orally.

(f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J Pharmacology*, 1983, 78(1), 67-574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests (a)–(f):

Test (a): $IC_{50}$ in the range, for example, 0.1–30 $\mu M$;

Test (b): $IC_{50}$ ($LTB_4$) in the range, for example, 0.1–40 $\mu M$, $IC_{50}$ ($TxB_2$) in the range, for example, 40–200 $\mu M$;

Test (c): oral $ED_{50}$ ($LTB_4$) in the range, for example, 5–200 mg/kg;

Test (d): $IC_{50}$ ($LTC_4$) in the range, for example, 0.001–1 $\mu M$, $IC_{50}$ ($PGE_2$) in the range, for example, 20–1000 $\mu M$;

Test (e): inhibition of inflammation in the range, for example, 0.3–100 $\mu g$ intradermally;

Test (f): $ED_{50}$ in the range, for example, 0.5–10 mg/kg i.v.

No overt toxicity or other untoward effects are present in tests (c), (e) and/or (f) when compounds of the formula I are administered at several multiples of their minimum inhibitory dose or concentration.

Thus, by way of example, the compound 2-methoxy-2-[3-(naphth-2-ylmethoxy)phenyl]but-1-yl methyl ether has an $IC_{50}$ of 0.5 $\mu M$ against $LTB_4$ and of $>40$ $\mu M$ against $TxB_2$ in test b), and an oral $ED_{50}$ of 30 mg/kg versus $LTB_4$ in test (c). In general those compounds of the formula I which are particularly preferred have an $IC_{50}$ of $<1$ $\mu M$ against $LTB_4$ and of $>40$ $\mu M$ against $TxB_2$ in test b), and an oral $ED_{50}$ of $<100$ mg/kg against $LTB_4$ in test c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an alcohol or an ether derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is an alcohol or ether derivative of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an alcohol or an ether derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of an alcohol or ether derivative of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a compound of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specifications Nos. 179619, 199543, 220066, 227241, 242167, 290145, 337765, 337766 and 337767, which are incorporated herein by way of reference.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°-20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point block apparatus; melting points for the end-products of the formula I were determined after recrystallisation from a conventional organic solvent such as ethanol, methanol, acetone, ether or hexane, alone or in admixture; and (viii) the specific rotation, $[\alpha]_t$, of plane polarised light was determined using the sodium D line (5890 Angstroms), at 20° C., and generally using sample concentrations of approximately 1 g/100 ml of solvent.

EXAMPLE 1

A mixture of 2-[3-(naphth-2-ylmethoxy)phenyl]butane-1,2-diol (0.6 g), sodium hydride (0.22 g of a 50% w/w dispersion in mineral oil) and dimethylformamide (10 ml) was stirred at ambient temperature for 5 minutes. Methyl iodide (0.29 ml) and 1,4,7,10,13-pentaoxacyclopentadecane (hereinafter 15-crown-5, 0.06 g) were added and the mixture was stirred at ambient temperature for 15 hours. The mixture was evaporated and the residue was partitioned between methylene chloride and water. The organic layer was separated, washed with water, dried ($MgSO_4$) and evaporated. The residue was purified by column chromatography using initially methylene chloride and then increasingly polar mixtures of methylene chloride and diethyl ether, up to a 19:1 v/v mixture, as eluent. There was thus obtained 2-methoxy-2-[3-(naphth-2-ylmethoxy)phenyl]-but-1-yl methyl ether as an oil which crystallised on standing (0.51 g, 87%), m.p. 47°-48° C.

The butane-1,2-diol starting material was obtained as follows:

Alkylation of a solution of 3-cyanophenol in dimethylformamide with 2-bromomethylnaphthalene in the presence of potassium carbonate gave 3-(naphth-2-ylmethoxy)benzonitrile, m.p. 91°-93° C. This material was treated with ethylmagnesium bromide using the procedure described in *Organic Synthesis, Collect.* Vol. III, p. 26, to give 3-(naphth-2-ylmethoxy)propiophenone, m.p. 56°-57° C.

A solution of this product (6 g) in tetrahydrofuran (12 ml) was added dropwise to a solution of isopropoxydimethylsilylmethyl magnesium chloride [prepared as described in *J. Org. Chem.*, 1983, 48, 2120 from chloromethylisopropoxydimethylsilane (8.2 ml) and magnesium powder (1.09 g) in tetrahydrofuran (2 ml)]. The mixture was stirred at ambient temperature for 1 hour, washed with saturated aqueous solution of ammonium chloride and then with a saturated aqueous solution of sodium chloride. The organic layer was separated, dried ($MgSO_4$) and evaporated to give 1-isopropoxydimethylsilyl-2-[3-(naphth-2-ylmethoxy)phenyl]butan-2-ol as a yellow oil.

A mixture of the product so obtained, sodium bicarbonate (1.73 g), hydrogen peroxide (18 ml, 30% w/v in water), methanol (60 ml) and tetrahydrofuran (60 ml) was heated to reflux for 15 hours. The mixture was evaporated to remove the organic solvents and the residue was extracted with diethyl ether. The organic layer was separated, washed with a saturated aqueous solution of sodium chloride, dried ($MgSO_4$) and evaporated. The residue was purified by column chromatography using initially methylene chloride and then increasingly polar mixtures of methylene chloride and acetone, up to a 9:1 v/v mixture, as eluent. There was thus obtained 2-[3-(naphth-2-ylmethoxy)phenyl]butane-1,2-diol (5.4 g, 81%), m.p. 100°–101° C.

EXAMPLE 2

A mixture of 3-(naphth-2-ylmethoxy)propiophenone (8.7 g), ethyl bromoacetate (5 ml), powdered zinc (2 g), a crystal of iodine and tetrahydrofuran (30 ml) was heated to 60° C. for 30 minutes. The mixture was poured into water (50 ml), neutralised by adding 2N aqueous hydrochloric acid, and extracted with diethyl ether. The organic extract was dried (MgSO4) and evaporated. The residue was purified by column chromatography using methylene chloride as eluent. There was thus obtained ethyl 3-hydroxy-3-[3-(naphth-2-ylmethoxy)phenyl]pentanoate (11.4 g, 100%), m.p. 61°–62° C.

EXAMPLE 3

The procedure described in Example 2 was repeated except that 3-(naphth-2-ylmethoxy)acetophenone was used in place of 3-(naphth-2-ylmethoxy)propiophenone and bromoacetonitrile was used in place of ethyl bromoacetate. There was thus obtained 3-hydroxy-3-[3-(naphth-2-ylmethoxy)phenyl]butyronitrile, m.p. 80°–81° C., which was methylated using the procedure described in Example 1 except that tetrahydrofuran was used in place of dimethylformamide. There was thus obtained 3-methoxy-3-[3-(naphth-2-ylmethoxy)phenyl]butyronitrile, m.p. 98°–99° C. (18% yield from the acetophenone).

3-(Naphth-2-ylmethoxy)acetophenone, m.p. 88°–89° C., used as a starting material was obtained by the alkylation of a solution of 3-hydroxyacetophenone in dimethylformamide with 2-bromomethylnaphthalene in the presence of potassium carbonate.

EXAMPLE 4

The methylation described in Example 1 was repeated except that the appropriate alcohol was used in place of 2-[3-naphth-2-ylmethoxy)phenyl]butane-1,2-diol. There were thus obtained the compounds described in the following table:

TABLE I

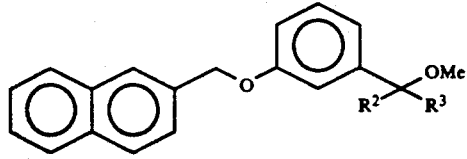

| Example 4: Compound No. | R² | R³ | m.p. (°C.) | Yield (%) |
|---|---|---|---|---|
| 1ᵃ | Me | CH₂OMe | 62–63 | 40 |
| 2ᵇ | H | CH₂OMe | 68–69 | 75 |
| 3ᶜ | CH₂OMe | CH₂OMe | oil | 92 |
| 4ᵈ | Et | (CH₂)₂OMe | 38–40 | 60 |
| 5ᵉ | H | (CH₂)₂OMe | 59–60 | 96 |
| 6ᶠ,ᵍ | Me | CH₂SMe | oil | 66 |
| 7ᶠ,ʰ | H | (CH₂)₂SMe | 54–55 | 79 |
| 8ᶠ,ⁱ | Me | (CH₂)₂SMe | 60–61 | 39 |
| 9ᶠ,ʲ | Me | CH(Me)SMe | 61–62 | 13 |
| 10ᵏ,ˡ | H | tetrahydrofuran-2-yl | 52–53 | 17 |
| 11ᵏ,ᵐ | H | tetrahydrofuran-2-yl | 42–43 | 76 |

Notes a The appropriate alcohol starting material was obtained as follows:

The appropriate acetophenone was treated with isopropoxydimethylsilylmethylmagnesium chloride using the procedure described in the portion of Example 1 which is concerned with the preparation of starting materials. After the oxidation step described therein there was obtained 2-[3-(naphth-2-ylmethoxyphenyl]-propane-1,2-diol, m.p. 119°–120° C.

b The appropriate alcohol starting material was obtained as follows:

3-(Naphth-2-ylmethoxy)benzaldehyde [prepared by the alkylation of 3-hydroxybenzaldehyde with 2-bromomethylnaphthalene in the presence of potassium carbonate] was treated with isopropoxydimethysilylmethylmagnesium chloride using the procedure described in the portion of Example 1 which is concerned with the preparation of starting materials. After the oxidation step described therein there was obtained 2-[3-(naphth-2-ylmethoxy)phenyl]ethane-1,2-diol, m.p. 121°–122° C.

c The appropriate alcohol starting material was obtained as follows:

The Grignard reagent was prepared from 3-(naphth-2-ylmethoxy)bromobenzene (3.13 g) in tetrahydrofuran (15 ml) and reacted with methoxyacetonitrile (0.17 g). The mixture was stirred at ambient temperature for 30 minutes, acidified with 6N aqueous hydrochloric acid and heated to reflux for 1 hour. The mixture was extracted with methylene chloride. The organic layer was dried. Evaporation left methoxymethyl 3-(naphth-2-ylmethoxy)phenyl ketone as an orange oil which crystallised on standing.

This ketone was used without further purification and was treated with isopropoxydimethylsilylmethylmagnesium chloride using the procedure described in the portion of Example 1 which is concerned with the preparation of starting materials. After the oxidation step described therein there was obtained 3-methoxy-2-[3-(naphth-2-ylmethoxy)phenyl]propane-1,2-diol as an oil.

Compound No. 3 displayed the following characteristic NMR signals (CDCl₃, δ values): 3.16(s, 3H), 3.34(s, 6H), 3.17(d of d, 4H), 5.23(s, 2H), 6.7–7.7(m, 7H), 7.7–8.0(m, 4H).

d The appropriate alcohol starting material was obtained as follows:

A mixture of ethyl 3-hydroxy-3-[3-(naphth-2-ylmethoxy)phenyl]pentanoate, lithium aluminium hydride and ether was stirred at ambient temperature for 1 hour. There was thus obtained 3-[3-naphth-2-ylmethoxy)phenyl]pentane-1,3-diol, m.p. 77°–78° C.

e The appropriate alcohol starting material was obtained as follows:

A mixture of 3-(naphth-2-ylmethoxy)benzaldehyde, ethyl bromoacetate and zinc was reacted using the procedure described in Example 2. There was thus obtained ethyl 3-hydroxy-3-[3-(naphth-2-ylmethoxy)phenyl)propionate which was reduced with lithium aluminium hydride using the conditions described in note d above to give 3-[3-(naphth-2-ylmethoxy)phenyl]-propane-1,3-diol as a colourless oil.

f Tetrahydrofuran was used in place of dimethylformamide as the solvent for the methylation reaction.

g The appropriate alcohol starting material was obtained as follows:

A Grignard reagent was prepared by heating a mixture of 3-(naphth-2-ylmethoxy)bromobenzene (3 g), magnesium powder (0.23 g) and tetrahydrofuran (12 ml) to 30° C. for 1.5 hours. The reagent was cooled to 20° C. and a solution of methylthioacetone [1 g, *Organic*

Synthesis, vol. 56, 72] in tetrahydrofuran (5 ml) was added dropwise. The mixture was heated to 30° C. for 15 hours, evaporated and the residue was partitioned between ethyl acetate and water. The organic layer was separated washed with a saturated aqueous sodium chloride solution, dried (MgSO₄) and evaporated. The residue was purified by column chromatography using a 7:3 v/v mixture of methylene chloride and diethyl ether as eluent. There was thus obtained 1-methylthio-2-[3-(naphth-2-ylmethoxy)phenyl]propan-2ol as an oil (1.2 g, 39%).

Compound No. 6 displayed the following characteristic NMR signals (CDCl₃, δ values): 1.66(s, 3H), 2.7(d, 1H), 2.9(d, 1H), 3.09(s, 3H), 5.25(s, 2H), 6.75–7.7(m, 7H), 7.7–8.0(m, 4H).

h The appropriate alcohol starting material was obtained using the procedure described in note g above except that 3-methylthiopropionaldehyde was used in place of methylthioacetone. There was thus obtained 3-methylthio-1-[3-naphth-2-ylmethoxy)phenyl]propan-1-ol as an oil (83%).

i The propan-1-ol described in note h above was oxidised on treatment with manganese dioxide. The ketone so obtained was treated with methylmagnesium bromide to give 1-methylthio-3-[3-(naphth-2-ylmethoxy)phenyl]butan-3-ol as an oil (50% over both stages).

j The appropriate alcohol starting material was obtained using the procedure described in note g above except that methyl 1-methylthioprop-2-yl ketone was used in place of methylthioacetone. There was thus obtained 2-methyl- 1-methylthio-3-[3-(naphth-2-ylmethoxyl)-phenyl]butan-3-ol as an oil (76%).

k The starting material, 1-[3-(naphth-2-ylmethoxy)-phenyl]-1-(tetrahydrofuran-2-yl)methanol, was a mixture of diastereoisomers, and was obtained in 21% yield using the procedure described in note g above except that 2-tetrahydrofuraldehyde [obtained by Swern oxidation of 2-tetrahydrofurfuryl alcohol using the procedure described in J. Org. Chem., 1978, 43, 2480] was used in placed of methylthioacetone.

After the methylation the diastereoisomers were separated by column chromatography using a 98:2 v/v mixture of methylene chloride and diethyl ether as eluent.

l This was the less polar isomer.

m This was the more polar isomer.

EXAMPLE 5

A mixture of 2-[3-(naphth-2-ylmethoxy)phenyl]bu-tane-1,2-diol (1 g), sodium hydride (0.13 g of a 50% w/w dispersion in mineral oil) and tetrahydrofuran (100 ml) was stirred at ambient temperature for 5 minutes. Methyl iodide (0.38 ml) was added and the mixture was stirred at ambient temperature for 15 hours. The mixture was evaporated and the residue was partitioned between methylene chloride and water. The organic layer was separated, washed with water, dried (MgSO₄) and evaporated. The residue was purified by column chromatography using initially methylene chloride and then increasingly polar mixtures of methylene chloride and diethyl ether, up to a 94:6 v/v mixture, as eluent. There was thus obtained 1-methoxy-2-[3-(naphth-2-ylmethoxy)phenyl]butan-2-ol (0.62 g, 57%), m.p. 47°–48° C.

EXAMPLE 6

A mixture of 2-[3-(naphth-2-ylmethoxy)phenyl]bu-tane-1,2-diol (1.05 g), tert-butyldimethylsilyl chloride (0.585 g), imidazole (0.55 g) and dimethylformamide (10 ml) was stirred at ambient temperature for 15 hours. The mixture was evaporated and the residue was purified by column chromatography using methylene chloride as eluent. There was thus obtained 1-tert-butyl-dimethylsilyloxy-2-[3-(naphth-2-ylmethoxy)phenyl]bu-tan-2-ol as a colourless oil (1.15 g, 81%).

This product was methylated using the procedure described in Example 1 except that tetrahydrofuran was used in place of dimethylformamide as the reaction solvent. There was thus obtained 2-methoxy-2-[3-naphth-2-ylmethoxy)phenyl]but-1-yl tert-butyldime-thylsilyl ether (0.825 g, 70%), m.p. 74°–76° C.

A mixture of a portion (0.62 g) of the product so obtained and tetrabutylammonium fluoride (4.27 ml of a 1M solution in tetrahydrofuran) was stirred at ambient temperature for 1 hour. The mixture was evaporated and the residue was partitioned between methylene chloride and water. The organic layer was separated, washed with water, dried (MgSO₄) and evaporated. The residue was purified by column chromatography using initially methylene chloride and then increasingly polar mixtures of methylene chloride and diethyl ether, up to a 9:1 v/v mixture, as eluent. There was thus obtained 2-methoxy-2-[3-(naphth-2-ylmethoxy)phenyl]bu-tan-1-ol (0.41 g, 86%), m.p. 80°–81° C.

EXAMPLE 7

The procedure described in Example 6 was repeated except that the appropriate diol was used in place of 2-[3-naphth-2-ylmethoxy)phenyl]butane-1,2-diol. There were thus obtained the compounds described in the following table:

TABLE II

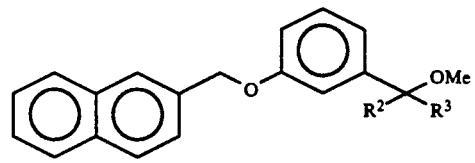

| Example 7: Compound No. | $R^2$ | $R^3$ | m.p. (°C.) | Yield (%) |
|---|---|---|---|---|
| 1ª | Me | $(CH_2)_2OH$ | 55–56 | 68 |
| 2ᵇ | $CH_2OMe$ | $CH_2OH$ | 71–72 | 90 |

Notes a 3-[3-(Naphth-2-ylmethoxy)phenyl]butane-1,3-diol used as a starting material was obtained, as an oil, by the reaction of 3-(naphth-2-ylmethoxy)acetophenone with ethyl bromoacetate using the procedure described in Example 2 followed by the reduction of the product so obtained with lithium aluminium hydride using the procedure described in Note d of Example 4.

b 3-Methoxy-2-[3-(naphth-2-ylmethoxy)phenyl]pro-pane-1,2-diol used as a starting material was obtained as described in Note c of Example 4.

EXAMPLE 8

A mixture of 2-methoxy-2-[3-(naphth-2-ylmethoxy)-phenyl]butan-1-ol (0.52 g), sodium hydride (0.1 g of a 50% w/w dispersion in mineral oil) and dimethylformamide (10 ml) was stirred at ambient temperature for 5 minutes. Ethyl iodide (0.25 ml) was added and the mixture was heated to 40° C. for 4 hours. The mixture was partitioned between methylene chloride and water. The organic layer was separated, washed with water, dried (MgSO₄) and evaporated. The residue was purified by column chromatography using initially methylene chloride and then increasingly polar mixtures of methylene chloride and diethyl ether, up to a 19:1 v/v mixture, as eluent. There was thus obtained as an oil which crystallised on standing 2-methoxy-2-[3-naphth-2-ylmethoxy)-phenyl]but-1-yl ethyl ether (0.47 g, 83%), m.p. 64°-65° C.

EXAMPLE 9

The procedure described in Example 8 was repeated except that the appropriate alkylating or acylating agent was used in place of ethyl iodide. There were thus obtained the compounds described in the following table:

TABLE III

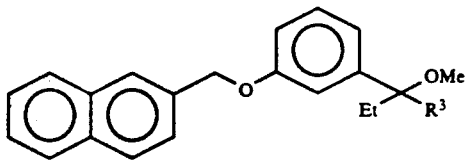

| Example 9: Compound No. | $R^3$ | m.p. (°C.) | Yield (%) |
|---|---|---|---|
| 1$^a$ | $CH_2O(CH_2)_2OMe$ | oil | 66 |
| 2$^b$ | $CH_2OAc$ | 74–75 | 62 |
| 3$^c$ | $CH_2SH$ | 79–80 | 50 | a 2-Methoxyethyl p-toluenesulphonate was used as the alkylating agent. The product displayed the following characteristic NMR signals (CDCl₃; δ values): 0.79(t, 3H), 1.92(m, 2H), 3.12(s, 3H), 3.30(s, 3H), 3.48(broad s, 4H), 3.73(d of d, 2H), 5.23(s, 2H), 6.7–7.7(m, 7H), 7.7–8.0(m, 4H).

b Acetyl chloride was used as the acylating agent. Triethylamine and methylene chloride were used in place of sodium hydride and dimethylformamide respectively.

c Following the general method described in *Tet. Let.*, 1981, 3119, a mixture of the butan-1-ol (1 g), thioacetic acid (0.365 ml), di-isopropyl azodicarboxylate (1 ml), triphenylphosphine (1.34 g) and tetrahydrofuran (21 ml) was cooled to 0° C. and stirred for 45 minutes. The mixture was filtered and evaporated. The crude residue was dissolved in diethyl ether (10 ml) and treated with lithium aluminium hydride (0.067 g) to give the desired product (0.42 g).

EXAMPLE 10

A mixture of 2-methoxy-2-[3-(naphth-2-ylmethoxy)-phenyl]prop-1-yl methyl sulphide (0.43 g), m-chloroperbenzoic acid (0.63 g) and methylene chloride (5 ml) was stirred at ambient temperature for 15 hours. The mixture was evaporated and the residue was purified by column chromatography using a 19:1 v/v mixture of methylene chloride and diethyl ether as eluent. There was thus obtained 2-methoxy-2-[3-(naphth-2-ylmethoxy)phenyl]prop-1-yl methyl sulphone (0.165 g, 35% m.p. 149°-150° C.

EXAMPLE 11

A mixture of 3-[3-(naphth-2-ylmethoxy)phenyl]pent-1-en-3-yl methyl ether (4.3 g) m-chloroperbenzoic acid (3.1 g) sodium bicarbonate (1.5 g) and methylene chloride (20 ml) was stirred at ambient temperature for 15 hours. The mixture was partitioned between diethyl ether and water and the organic layer was separated, dried (MgSO₄) and evaporated. The residue was purified by column chromatography using a 4:1 v/v mixture of methylene chloride and petroleum ether (b.p. 60°–80° C.) as eluent. There were thus obtained: a less polar isomer as a colourless oil (0.41 g, 9%) and a more polar isomer (0.13 g, 3%), m.p. 45°–47° C., of 1-[3-(naphth-2-ylmethoxy)phenyl]-1-oxiranylprop-1-yl methyl ether. The less polar isomer displayed the following characteristic NMR signals (CDCl₃); δ values): 0.82(t, 3H), 1.5–2.1(m, 2H), 2.69(d, 2H), 3.1(t, 1H), 3.25(s, 3H), 5.22(s, 2H), 6.8–7.88(m, 11H).

The 3-[3-(naphth-2-ylmethoxy)phenyl]pent-1-en-3-yl methyl ether starting material was obtained as follows:

Vinylmagnesium bromide (76 ml of a 1M solution in tetrahydrofuran) was added dropwise to a solution of 3-(naphth-2-ylmethoxy)propiophenone (17.4 g) in tetrahydrofuran (150 ml) and the mixture was stirred at ambient temperature for 30 minutes. The mixture was poured into a mixture of water and ice (total volume 1 liter containing ammonium chloride (20 g). The mixture was extracted with diethyl ether, dried (MgSO₄) and evaporated. There was thus obtained 3-[3-(naphth-2-ylmethoxy)phenyl]pent-1-en-3-ol as a yellow oil (19.4 g) which was used without further purification.

A portion (1.6 g) of this alcohol was methylated using the procedure described in Example 1 except that tetrahydrofuran was used in place of dimethylformamide as the reaction solvent. There was thus obtained 3-[3-(naphth-2-ylmethoxy)phenyl]pent-1-en-3-yl methyl ether (0.75 g, 45%), m.p. 39°–40° C.

EXAMPLE 12

A mixture of 2-(3-hydroxyphenyl)-2-methoxybut-1-yl methyl ether (0.5 g), 3-phenylprop-2-ynyl bromide (0.75 g), potassium carbonate (0.37 g) and dimethylformamide (6 ml) was stirred at ambient temperature for 15 hours. The mixture was partitioned between methylene chloride and water. The organic layer was washed with a saturated aqueous sodium chloride solution, dried (MgSO₄) and evaporated. The residue was purified by column chromatography using a 49:1 v/v mixture of methylene chloride and diethyl ether as eluent. There was thus obtained 2-methoxy-2-[3-(3-phenylprop-2-ynyloxy)phenyl]but-1-yl methyl ether as a colourless oil (0.68 g, 85%).

NMR Spectrum (CDCl₃; δ values) 0.79(t, 3H), 1.7–2.1(m, 2H), 3.15(s, 3H), 3.31(s, 3H), 3.65(m, 2H), 4.92(s, 2H), 6.8–7.5(m, 9H).

The 2-(3-hydroxyphenyl)-2-methoxybut-1-yl methyl ether starting material was obtained as follows:

3-Methoxymethoxybenzaldehyde was prepared from 3-hydroxybenzaldehyde and dimethoxymethane using the method described in *Synthesis*, 1976, 244. Ethylmagnesium bromide (161 ml of a 3M solution in diethyl ether) was added to a solution of 3-methoxymethoxybenzaldehyde (73 g) in diethyl ether (150 ml) which had been cooled to 0° C. The mixture was allowed to warm to ambient temperature and was stirred for 1 hour. The mixture was poured into a mixture of diethyl ether (2 liters) and 1N aqueous hydrochloric acid (500 ml). The organic layer was washed with water and with a saturated aqueous sodium chloride solution, dried (MgSO₄) and evaporated to give, as an oil (83.8 g, 97%), α-ethyl-3-methoxymethoxybenzyl alcohol.

A mixture of the product so obtained, manganese dioxide (300 g) and methylene chloride (1.1 liter) was stirred at ambient temperature for 15 hours, filtered through silica gel and evaporated. There was thus obtained, as an oil (50 g, 60%), 3-methoxymethoxypropiophenone. A portion (19.4 g) of this product was reacted with isopropoxydimethylsilylmethylmagnesium chloride using the procedure described in the portion of Example 1 which is concerned with the preparation of starting materials. The product so obtained was treated with hydrogen peroxide using the method described therein to give, as a colourless oil (26.6 g, 74%), 2-(3-methoxymethoxyphenyl)butane-1,2-diol.

A portion (16.3 g) of this diol was methylated using the procedure described in Example 1 to give 2-methoxy-2-(3-methoxymethoxyphenyl)but-1-yl methyl ether (16.3 g) and a mixture of this material, concentrated hydrochloric acid (10 ml), isopropanol (40 ml) and tetrahydrofuran (160 ml) was stirred at ambient temperature for 15 hours. The mixture was evaporated and the residue was partitioned between ethyl acetate and water. The organic layer was washed with a saturated aqueous sodium chloride solution, dried (MgSO₄) and evaporated. The residue was purified by column chromatography using initally methylene chloride and then increasingly polar mixture of methylene chloride and diethyl ether, up to a 17:3 v/v mixture, as eluent. There was thus obtained 2-(3-hydroxyphenyl)-2-methoxybut-1-yl methyl ether (6.9 g, 51%), m.p. 74°–75° C.

EXAMPLE 13

The procedure described in Example 12 was repeated except that the appropriate phenol was used in place of 2-(3-hydroxyphenyl)-2-methoxybut-1-yl methyl ether. There were thus obtained the compounds described in the following table:

TABLE IV $$\text{Ph}-C\equiv C-CH_2-O-Ar^2-\underset{R^3}{\underset{|}{C}}-R^2$$
with OMe on the central C

| Ex. 13 Compd. No. | Ar² | R² | R³ | m.p. (°C.) | Yield (%) |
|---|---|---|---|---|---|
| 1ᵃ | 1,3-phenylene | CH₂OMe | CH₂CH₂OMe | oil | 93 |
| 2ᵇ | 1,3-phenylene | CH₂OMe | CH₂CH₂OH | oil | 83 |
| 3ᶜ | 1,3-phenylene | CH₂OMe | CH₂OH | oil | 80 |
| 4ᵈ | 5-fluoro-1,3-phenylene | Me | CH(Me)OMe | oil | 93 |
| 5ᵉ | 5-fluoro-1,3-phenylene | Et | CH₂OMe | oil | 83 |
| 6ᶠ | 3,5-pyridylene | Et | CH₂OMe | oil | 25 |

NOTES a. The product displayed the following characteristic NMR signals (CDCl₃, delta values) 2.1–2.4(m, 2H), 3.16(s, 3H), 3.24(s, 3H), 3.31(s, 3H), 3.25–3.55(m, 2H), 3.65(s, 2H), 4.91(s, 2H), 6.85–7.5(m, 9H).

The 3-(3-hydroxyphenyl)-3,4-dimethoxybut-1-yl methyl ether, used as a starting material, was obtained as follows:

A mixture of 3-benzyloxybenzaldehyde (21.2 g, J. Chem. Soc., 1957, 513), ethyl bromoacetate (25 g), powdered zinc (9.8 g), a crystal of iodine and tetrahydrofuran (50 ml) was heated to reflux to initiate the reaction. The mixture was then stirred at ambient temperature for 4 hours. The mixture was evaporated and the residue was purified by column chromatography using a 9:1 v/v mixture of methylene chloride and diethyl ether as eluent. There was thus obtained ethyl 3-(3-benzyloxyphenyl)-3-hydroxypropionate (21.7 g, 80%), as an oil.

A solution of the compound so obtained in diethyl ether (10 ml) was added to a stirred suspension of lithium aluminium hydride (3.45 g) in diethyl ether (700 ml) and the mixture was stirred at ambient temperature for 30 minutes. Ethyl acetate (30 ml) and water (30 ml) were added slowly in succession. The mixture was filtered and the organic phase was separated and evaporated. The residue was triturated in pentane and there was thus obtained 3-(3-benzyloxyphenyl)propane-1,3-diol (18.8 g, 91%), m.p. 78°–79° C.

A mixture of a portion (8.33 g) of the product so obtained, manganese dioxide (80 g) and acetone (400 ml) was stirred at ambient temperature for 15 hours. The mixture was filtered and the filtrate was evaporated. The residue was purified by column chromatography using a 9:1 v/v mixture of methylene chloride and diethyl ether as eluent. There was thus obtained 3-(3-benzyloxyphenyl)-3-oxopropan-1-ol (1.73 g, 20%), as an oil.

After repetition of the above reaction and using the procedure described in the second and third paragraphs of the portion of Example 1 which is concerned with the preparation of starting materials, the ketone so obtained (2.56 g) was reacted with isopropoxydimethylsilylmethylmagnesium chloride and the product was oxidised with hydrogen peroxide. There was thus obtained 2-(3-benzyloxyphenyl)butane-1,2,4-triol (0.7 g, 24%), as an oil.

Using the procedure described in Example 1, the triol so obtained was reacted with methyl iodide to give 2-(3-benzyloxyphenyl)-2,4-dimethoxybut-1-yl methyl ether (0.73 g, 91%), as an oil.

A mixture of the product so obtained, 10% palladium-on-charcoal catalyst (0.08 g) and ethanol (10 ml) was stirred under an atmosphere of hydrogen for 6 hours. The mixture was filtered and the filtrate was evaporated. The residue was purified by column chromatography using a 9:1 v/v mixture of methylene chloride and acetone as eluent. There was thus obtained the required starting material (0.49 g, 92%), as an oil.

NMR Spectrum (CDCl₃, delta values) 2.1–2.3(m, 3H), 3.18(s, 3H), 3.28(s, 3H), 3.1–3.5(m, 5H), 3.65(s, 2H), 5.29(s, 1H), 6.68–7.3(m, 4H).

b. The product displayed the following characteristic NMR signals (CD₃SOCD₃, delta values) 1.98–2.15(m, 2H), 3.1(s, 3H), 3.23(s, 3H), 3.25–3.5(m, 2H), 3.63(s, 2H), 4.24(t, 1H), 5.05(s, 2H), 6.9–7.5(m, 9H).

c. The product displayed the following characterisitic NMR signals (CDCl₃, delta values) 3.23(s, 3H), 3.4(s, 3H), 3.77(s, 2H), 3.9–4.1(m, 1H), 4.92(s, 2H), 6.8–7.5(m, 9H).

The 2-(3-hydroxyphenyl)-2,3-dimethoxypropan-1-ol, used as a starting material, was obtained as follows:

Methoxyaceonitrile (14 g) in tetrahydrofuran (10 ml) was added to a solution of 3-benzyloxyphenylmagnesium bromide [prepared by heating a mixture of 3-benzyloxybromobenzene (52.6 g), magnesium powder (4.8 g) and tetrahydrofuran (250 ml) to 60° C. for 3 hours] in tetrahydrofuran and the mixture was heated to 60° C. for 30 minutes. The mixture was cooled to ambient temperature and acidified by the addition of 3N hydrochloric acid solution (250 ml). The mixture was extracted with diethyl ether. The organic phase was washed with water and with a saturated aqueous sodium chloride solution, dried (MgSO$_4$) and evaporated. The residue was purified by column chromatography using a 19:1 v/v mixture of methylene chloride and diethyl ether as eluent. There was thus obtained 3-benzyloxyphenyl methoxymethyl ketone (32.3 g, 63%), as an orange oil.

Using the procedure described in the second and third paragraphs of the portion of Example 1 which is concerned with the preparation of starting materials, a portion (10 g) of the ketone so obtained was reacted with isopropoxydimethylsilylmethylmagnesium chloride and the product so obtained was oxidised with hydrogen peroxide. There was thus obtained 2-(3-benzyloxyphenyl)-3-methoxypropane-1,2-diol (9.04 g, 80%), as an oil.

Using the three-step procedure described in Example 6, a portion (5.76 g) of the product so obtained was methylated. There was thus obtained 2-(3-benzyloxyphenyl)-2,3-dimethoxypropan-1-ol (4.71 g, 77%), as an oil.

Using the procedure described in the second last paragraph of Note a. above, the product so obtained was hydrogenolysed. There was thus obtained the required starting material (3.3 g, 99%), as an oil.

NMR Spectrum (CDCl$_3$, delta values) 3.08(s, 3H), 3.25(s, 3H), 3.64(d of d's, 4H), 6.5–7.25(m, 4H).

d. The product displayed the following characteristic NMR signals (CDCl$_3$, delta values) 1.1(d, 3H), 1.5(s, 3H), 3.06(s, 3H), 3.09(s, 3H), 3.25(q, 1H), 4.9(s, 2H), 6.5–7.0(m, 3H), 7.2–7.5(m, 5H).

The (2RS,3SR)-2-(5-fluoro-3-hydroxyphenyl)-2-methoxybut-3-yl methyl ether, used as a starting material, was obtained as follows:

A mixture of benzyl alcohol (10 g), sodium hydride (4.4 g of a 50% w/w dispersion in mineral oil) and dimethylacetamide (180 ml) was stirred at ambient temperature for 1 hour; 1-bromo-3,5-difluorobenzene (10.65 ml) was added and the exothermic reaction mixture was stirred for 2 hours. The mixture was evaporated and the residue was partitioned between methylene chloride and water. The organic layer was separated, washed with water, dried (MgSO$_4$) and evaporated. The residue was purified by column chromatography using a 20:1 v/v mixture of petroleum ether (b.p. 60°–80° C.) and ethyl acetate as eluent. There was thus obtained, as a liquid, benzyl 3-bromo-5-fluorophenyl ether (19.5 g, 75%).

A solution of 3-tert-butyldimethylsilyloxybutan-2-one (5.56 g; prepared by reacting 3-hydroxybutan-2-one with tert-butyldimethylsilyl chloride in diethyl ether and using imidazole as a suitable base) in tetrahydrofuran (5 ml) was added to a solution of 3-benzyloxy-5-fluorophenylmagnesium bromide [prepared by heating a mixture of benzyl 3-bromo-5-fluorophenyl ether (6.7 g), magnesium powder (0.58 g) and tetrahydrofuran (50 ml) to 40° C. for 1 hour] in tetrahydrofuran (50 ml) and the mixture was stirred at ambient temperature for 2.5 hours. The mixture was evaporated and the residue was partitioned between diethyl ether and water. The organic phase was washed with a saturated aqueous sodium chloride solution, dried (MgSO$_4$) and evaporated. The residue was purified by column chromatography using a 3:2 v/v mixture of petroleum ether (b.p. 40°–60° C.) and methylene chloride as eluent. There was thus obtained an erythro isomer, (2RS,3SR)-2-(3-benzyloxy-5-fluorophenyl)-3-(tert-butyldimethylsilyloxy)butan-2-ol (3.8 g, 41%), as an oil; and a threo isomer, the corresponding (2RS,3RS)-isomer (1.73 g, 18%), as an oil.

Using the conditions described in the last paragraph of Example 6, the tert-butyldimethylsilyl group was removed from the erythro isomer so obtained. There was thus obtained (2RS,3SR)-2-(3-benzyloxy-5-fluorophenyl)butane-2,3-diol (2.66 g, 98%), as an oil.

Using the procedure described in Example 1, the product so obtained was reacted with methyl iodide to give (2RS,3SR)-2-(3-benzyloxy-5-fluorophenyl)-2-methoxybut-3-yl methyl ether (2.8 g, 96%), as an oil.

Using the procedure described in the second last paragraph of Note a. above, a portion (1.38 g) of the product so obtained was hydrogenolysed. There was thus obtained the required starting material (0.836 g, 84%), m.p. 107°–108° C.

e. The product displayed the following characteristic NMR signals (CDCl$_3$, delta values) 0.8(t, 3H), 1.7–2.04(m, 2H), 3.17(s, 3H), 3.33(s, 3H), 3.59(d, 1H), 3.65(d, 1H), 4.93(s, 2H), 6.67(m, 1H), 6.75(m, 1H), 6.87(t, 1H), 7.3–7.5(m, 5H).

The 2-(5-fluoro-3-hydroxyphenyl)-2-methoxybut-1-yl methyl ether, used as a starting material, was obtained as follows:

A mixture of benzyl alcohol (2.16 g), sodium hydride (50% w/w dispersion in mineral oil, 0.96 g) and dimethylacetamide (40 ml) was stirred at ambient temperature for 30 minutes. 3,5-Difluorobenzonitrile (2.78 g) was added slowly and an exothermic reaction ensued. The mixture was stirred at ambient temperature for 1 hour and then partitioned between ethyl acetate and water. The organic phase was washed with water and with a saturated aqueous sodium chloride solution, dried (MgSO$_4$) and evaporated. The residue was purified by column chromatography using increasingly polar mixtures of petroleum ether (b.p. 40°–60° C.) and toluene as eluent. There was thus obtained 3-benzyloxy-5-fluorobenzonitrile (3.65 g, 80%), as an oil.

Using the procedures described in the portion of Example 1 which is concerned with the preparation of starting materials, the benzonitrile so obtained was reacted with ethylmagnesium bromide, the resultant ketone was reacted with isopropoxydimethylsilylmethylmagnesium chloride and the resultant product was oxidised with hydrogen peroxide. There was thus obtained 2-(3-benzyloxy-5-fluorophenyl)butane-1,2-diol in 58% yield, as an oil.

Using the procedure described in Example 5, the diol so obtained was reacted with methyl iodide to give 2-(3-benzyloxy-5-fluorophenyl)-2-methoxybut-1-yl methyl ether in 88% yield, as an oil.

A mixture of the product so obtained (26.3 g), 10% palladium-on-charcoal catalyst (1.5 g) and ethanol (300 ml) was stirred under an atmosphere of hydrogen for 4 hours. The mixture was filtered and the filtrate was evaporated. There was thus obtained the required starting material (18.8 g, 99%), m.p. 61°–62° C.

f. The product displayed the following characteristic NMR signals (CD$_3$SOCD$_3$, delta values) 0.7(t, 3H), 1.7–2.0(m, 2H), 3.1(s, 3H), 3.2(s, 3H), 3.65(s, 2H), 5.2(s, 2H), 7.4(m, 6H), 8.2(m, 1H), 8.3(m, 1H).

The 2-(5-hydroxypyrid-3-yl)-2-methoxybut-1-yl methyl ether, used as a starting material, was obtained as follows:

Sodium hydride (50% w/w dispersion in mineral oil, 5 g) was added portionwise to a mixture of benzyl alcohol (12.4 g) and dimethylformamide (150 ml) which had been cooled to 0° C. The mixture was allowed to warm to ambient temperature and was stirred for 1 hour. 3,5-Dibromopyridine (25.2 g) was added and the mixture was heated to 60° C. for 2 hours. The mixture was cooled to ambient temperature and partitioned between ethyl acetate and a dilute aqueous potassium carbonate solution. The organic layer was washed with a dilute aqueous hydrochloric acid solution and with a saturated aqueous sodium chloride solution, dried (MgSO$_4$) and evaporated. The residue was a red oil which on trituration under petroleum ether (b.p. 60°–80° C.) gave 5-benzyloxy-3-bromopyridine (18.6 g, 67%), m.p. 65°–67° C. A solution of a portion (11.5 g) of this product in diethyl ether (500 ml) was cooled to −50° C. and n-butyllithium (1.5M in hexane, 32 ml) was added dropwise. The mixture was stirred at −50° C. for 20 minutes, further cooled to −60° C. and a solution of ethyl methoxymethyl ketone (5 g; *J. Amer. Chem. Soc.*, 1946, 68, 2339) in diethyl ether (50 ml) was added. The mixture was stirred at −60° C. for 1 hour and at −30° C. for 30 minutes. A saturated aqueous ammonium chloride solution (200 ml) was added and the mixture was extracted with ethyl acetate (3×50 ml). The combined organic extracts were washed with a saturated aqueous sodium chloride solution, dried (MgSO$_4$) and evaporated. The residue was purified by column chromatography using a 7:3 v/v mixture of toluene and ethyl acetate as eluent. The oil so obtained was triturated under a mixture of petroleum ether (b.p. 60°–80° C.) and diethyl ether. There was thus obtained 2-(5-benzyloxypyrid-3-yl)-1-methoxybutan-2-ol (5.84 g, 47%), m.p. 83°–84° C.

After repetition of the above step, a mixture of the product so obtained (6.5 g), sodium hydride (55% w/w dispersion in mineral oil, 1.1 g) and dimethylformamide (60 ml) was stirred at −5° C. for 30 minutes. Methyl iodide (1.56 ml) was added and the mixture was stirred at −5° C. for 90 minutes. The mixture was partitioned between ethyl acetate and ice-cold water. The organic phase was washed with a saturated aqueous sodium chloride solution, dried (MgSO$_4$) and evaporated. The residue was purified by column chromatography using a 5:3 v/v mixture of toluene and ethyl acetate as eluent. There was thus obtained 2-(5-benzyloxypyrid-3-yl)-2-methoxybut-1-yl methyl ether (6.42 g, 94%), as an oil.

NMR Spectrum (CDCl$_3$, delta values) 0.8(t, 3H), 1.7–2.1(m, 2H), 3.15(s, 3H), 3.3(s, 3H), 3.6(d, 2H), 5.13(s, 2H), 7.3–7.5(m, 6H), 8.2(d, 1H), 8.3(d, 1H).

A mixture of a portion of (6 g) of the product so obtained, 10% palladium-on-charcoal catalyst (0.6 g) and isopropanol (60 ml) was stirred under an atmosphere of hydrogen for 5 hours. The mixture was filtered and the filtrate was evaporated. The residue was triturated under petroleum ether (b.p. 60°–80° C.). There was thus obtained the required starting material (3.7 g, 88%), m.p. 87°–88° C.

EXAMPLE 14

Using the procedure described in Example 12, 3-(3-hydroxyphenyl)-3,4-dimethoxybutan-1-ol was reacted with 2-bromomethylnaphthalene to give 3,4-dimethoxy-3-[3-(naphth-2-ylmethoxy)phenyl]butan-1-ol in 87% yield, m.p. 64°–65° C.

The 3-(3-hydroxyphenyl)-3,4-dimethoxybutan-1-ol, used as a starting material, was obtained as follows:

A mixture of 3-(3-benzyloxyphenyl)-3-oxopropan-1-ol (2.07 g), dihydropyran (1.1 g), an acidic ion-exchange resin (0.2 g, 'Amberlyst 15') and methylene chloride (5 ml) was stirred at ambient temperature for 4 hours. The mixture was filtered and filtrate was evaporated. The residue was purified by column chromatography using a 50:1 v/v mixture of methylene chloride and acetone as eluent. There was thus obtained 3-benzyloxyphenyl-2-tetrahydropyran-2-yloxymethyl ketone (1.85 g, 67%), as an oil.

Using the procedure described in the second and third paragraphs of the portion of Example 1 which is concerned with the preparation of starting materials, the ketone so obtained was reacted with isopropoxydimethylsilylmethylmagnesium chloride and the product was oxidised with hydrogen peroxide. There was thus obtained 2-(3-benzyloxyphenyl)-4-tetrahydropyran-2-yloxybutane-1,2-diol (1.65 g, 83%), as an oil.

Using the procedure described in Example 1, the diol so obtained was reacted with methyl iodide to give 2-(3-benzyloxyphenyl)-2-methoxy-4-tetrahydropyran-2-yloxybut-1-yl methyl ether (1.61 g, 91%), as an oil.

A mixture of the product so obtained, acidic ion-exchange resin (0.2 g, 'Amberlyst 15') and methanol (15 ml) was heated to 45° C. for 2 hours. The mixture was filtered and the filtrate was evaporated. There was thus obtained 3-(3-benzyloxyphenyl)-3,4-dimethoxybutan-1-ol (1.3 g, 99%), which was used without further purification.

A mixture of the product so obtained, 10% palladium-on-charcoal catalyst (0.3 g) and ethanol (15 ml) was stirred under an atmosphere of hydrogen for 6 hours. The mixture was filtered and the filtrate was evaporated. The residue was purified by column chromatography using a 4:1 v/v mixture of methylene chloride and acetone as eluent. There was thus obtained 3-(3-hydroxyphenyl)-3,4-dimethoxybutan-1-ol (0.73 g, 78%), as an oil.

NMR Spectrum (CDCl$_3$, delta values) 1.8–2.1(m, 2H), 3.08(s, 3H), 3.25(s, 3H), 3.1–3.5(m, 2H), 3.79(s, 2H), 4.21(t, 1H), 6.5–7.25(m, 4H).

EXAMPLE 15

Using the procedure described in Example 12, (2RS,3SR)-2-(5-fluoro-3-hydroxyphenyl)-2-methoxybutan-3-ol was reacted with 2-bromomethylnaphthalene to give (2RS,3SR)-2-[5-fluoro-3-(naphth-2-ylmethoxy)phenyl]-2-methoxybutan-3-ol in 94% yield, m.p. 62°–63° C.

The (2RS,3RS)-2-(5-fluoro-3-hydroxyphenyl)-2-methoxybutan-3-ol, used as a starting material, was obtained as follows:

Using the procedure described in the last two paragraphs of Example 6, erythro- or (2RS,3SR)-2-(3-benzyloxy-5-fluorophenyl)-3-(tert-butyldimethylsilyloxy)-butan-2-ol (5 g) was reacted with methyl iodide and the tert-butyldimethylsilyl group was removed from the product obtained. There was thus obtained (2RS,3SR)-2-(3-benzyloxy-5-fluorophenyl)-2-methoxybutan-3-ol (3.9 g, 99%), as an oil.

Using the procedure described in the second last paragraph of Note a. below Table IV in Example 13, the product so obtained was hydrogenolysed. There was thus obtained the required starting material (0.07 g, 76%), m.p. 84°–85° C.

EXAMPLE 16

Using the procedure described in Example 8, (2RS,3SR)-2-(5-fluoro-3-(naphth-2-ylmethoxy)phenyl]-2-methoxybutan-3-ol was reacted with methyl iodide to give (2RS,3SR)-2-(5-fluoro-3-(naphth-2-ylmethoxy)phenyl]-2-methoxybut-3-yl methyl ether in 60% yield, m.p. 75°-76° C.

The reaction described immediately above was repeated except that prop-2-ynyl bromide was used in place of methyl iodide. There was thus obtained (2RS,3SR)-2-(5-fluoro-3-(naphth-2-ylmethoxy)phenyl]-2-methoxybut-3-yl prop-2-ynyl ether in 76% yield, m.p. 58°-59° C.

EXAMPLE 17

Using the procedure described in Example 8, 2-methoxy-2-[3-(naphth-2-ylmethoxy)phenyl]butan-1-ol (Example 6) was reacted with prop-2-ynyl bromide to give 2-methoxy-2-[3-(naphth-2-ylmethoxy)phenyl]but-1-yl prop-2-ynyl ether in 92% yield, m.p. 54° C.

EXAMPLE 18

The procedure described in Example 12 was repeated except that (E)-cinnamyl bromide was used in place of 3-phenylprop-2-ynyl bromide. There was thus obtained 2-(3-(E)-cinnamyloxyphenyl)-2-methoxybut-1-yl methyl ether in 70% yield, as an oil.

NMR Spectrum (CDCl$_3$, delta values) 0.8(t, 3H), 1.8-2.1(m, 2H), 3.15(s, 3H), 3.3(s, 3H), 3.64(d of d's, 2H), 4.7(d, 2H), 6.2-7.5(m, 11H).

EXAMPLE 19

Using the procedure described in Note c. below Table III in Example 9, 2-[3-(3-phenylprop-2-ynyloxy)phenyl]-2,3-dimethoxypropan-1-ol (Example 13, Compound No. 3) was reacted with thioacetic acid. The mercaptan so obtained was reacted with methyl iodide using the conditions described in Example 1. There was thus obtained 2-methoxy-3-methylthio-2-[3-(3-phenylprop-2-ynyloxy)phenyl]prop-1-yl methyl ether in 27% overall yield, as an oil.

NMR Spectrum (CDCl$_3$, delta values) 1.91(s, 3H), 3.0(m, 2H), 3.14(s, 3H), 3.37(s, 3H), 3.85(s, 2H), 4.92(s, 2H), 6.85-7.5(m, 9H).

EXAMPLE 20

Using the procedure described in Example 12, 2-(3-hydroxyphenyl)-2-methoxy-4-(2,5,5-trimethyl-1,3-dioxan-2-yl)but-1-yl methyl ether was reacted with 3-phenylprop-2-ynyl bromide to give 2-methoxy-2-[3-(3-phenylprop-2-ynyloxy)phenyl]-4-(2,5,5-trimethyl-1,3-dioxan-2-yl)but-1-yl methyl ether in 85% yield, as an oil.

A mixture of a portion (0.54 g) of the product so obtained, acetone (15 ml) and 6N hydrochloric acid solution (1 ml) was stirred at ambient temperature for 15 hours. The mixture was evaporated and the residue was partitioned between diethyl ether and water. The organic phase was washed with water, dried (MgSO$_4$) and evaporated. The residue was purified by column chromatography using a 25:1 v/v mixture of methylene chloride and acetone as eluent. There was thus obtained 3,4-dimethoxy-3-[3-(3-phenylprop-2-ynyloxy)phenyl]butyl methyl ketone (0.42 g, 96%), as an oil.

NMR Spectrum (CDCl$_3$, delta values) 2.04(s, 3H), 1.97-2.27(m, 4H), 3.17(s, 3H), 3.29(s, 3H), 3.62(s, 2H), 4.92(s, 2H), 6.85-7.25(m, 9H).

The 2-(3-hydroxyphenyl)-2-methoxy-4-(2,5,5-trimethyl-1,3-dioxan-2-yl)but-1-yl methyl ether, used as a starting material, was obtained as follows:

A solution of 3-benzyloxyphenyl methoxymethyl ketone (3.2 g) in tetrahydrofuran (2 ml) was added to a solution of 2-(2,5,5-trimethyl-1,3-dioxan-2-yl)ethylmagnesium bromide [prepared by heating a mixture of 2-(2,5,5-trimethyl-1,3-dioxan-2-yl)ethyl bromide (3.55 g), magnesium powder (1.08 g) and tetrahydrofuran (25 ml) to 40° C. for 30 minutes] in tetrahydrofuran (25 ml) which had been cooled to ambient temperature. The mixture was stirred at ambient temperature for 15 hours and evaporated. The residue was partitioned between methylene chloride and water. The organic phase was washed with water, dried (MgSO$_4$) and evaporated. The residue was purified by column chromatography using a 10:1 v/v mixture of methylene chloride and diethyl ether as eluent. There was thus obtained 2-(3-benzyloxyphenyl)-1-methoxy-4-(2,5,5-trimethyl-1,3-dioxan-2-yl)butan-2-ol (2.85 g, 55%), as an oil.

Using the procedure described in Example 1, the product so obtained was reacted with methyl iodide. There was thus obtained 2-(3-benzyloxyphenyl)-2-methoxy-4-(2,5,5-trimethyl-1,3-dioxan-2-yl)but-1-yl methyl ether (2.9 g, 98%), as an oil.

Using the procedure described in the second last paragraph of Note a. below Table IV in Example 13, the product so obtained was hydrogenolysed. There was thus obtained the required starting material (1.84 g, 80%), as an oil.

EXAMPLE 21

Using the procedure described in Example 12, 2-(5-fluoro-3-hydroxyphenyl)-2-methoxybut-1-yl methyl ether was reacted with 2-bromomethyl-7-fluoronaphthalene to give 2-[5-fluoro-3-(7-fluoronaphth-2-ylmethoxy)phenyl]-2-methoxybut-1-yl methyl ether in 76% yield, as an oil.

NMR Spectrum (CDCl$_3$, delta values) 0.79(t, 3H), 1.7-2.0(m, 2H), 3.14(s, 3H), 3.32(s, 3H), 3.57(d, 1H), 3.64(d, 1H), 5.2(s, 2H), 6.64(m, 1H), 6.73(m, 1H), 6.86(t, 1H), 7.2-7.9(m, 6H).

The 2-bromomethyl-7-fluoronaphthalene used as a starting material was obtained as follows:

3-Fluorobenzyl chloride was reacted with acetylacetaldehyde dimethyl acetal using the procedure described for the corresponding reaction of 3-methylbenzyl chloride (*Synthesis*, 1974, 566). There was thus obtained 4-(3-fluorophenyl)-3-hydroxy-3-methylbutanal dimethyl acetal (b.p. 125°-135° C. at 0.25 mm Hg). A mixture of the material so obtained (15 g), glacial acetic acid (60 ml) and hydrobromic acid (48% w/v. 48 ml) was heated on a steam bath for 1 hour. The mixture was evaporated and the residue was purified by column chromatography using petroleum ether (b.p. 60°-80° C.) as eluent. There was thus obtained 7-fluoro-2-methylnaphthalene (4 g).

A mixture of 7-fluoro-2-methylnaphthalene (3 g), N-bromosuccinimide (3.3 g), 2,2'-azobisisobutyronitrile (0.2 g) and carbon tetrachloride (100 ml) was heated to reflux and irradiated with the light from a 275 watt bulb for 1 hour. The mixture was cooled to ambient temperature and filtered. The filtrate was evaporated and the residue was purified by column chromatography using a 19:1 v/v mixture of petroleum ether (b.p. 60°-80° C.) and toluene as eluent. There was thus obtained 2-bromomethyl-7-fluoronaphthalene (2.8 g), m.p. 62° C.

EXAMPLE 22

Using the procedure described in Example 12, 2-(5-hydroxypyrid-3-yl)-2-methoxybut-1-yl methyl ether (0.21 g) was reacted with 2-bromomethylnaphthalene (0.25 g) to give 2-methoxy-2-[5-(naphth-2-ylmethoxy)-pyrid-3-yl]but-1-yl methyl ether (0.13 g, 37%), as an oil.

NMR Spectrum (CD$_3$SOCD$_3$, delta values) 0.65(t, 3H), 1.7-2.0(m, 2H), 3.1(s, 3H), 3.2(s, 3H), 3.6(s, 2H), 5.4(s, 2H), 7.4(m, 1H), 7.5-7.65(m, 3H), 7.9-8.0(m, 4H), 8.15(d, 1H), 8.3(d, 1H).

EXAMPLE 23

The reaction described in Example 21 was repeated except that (+)-2-(5-fluoro-3-hydroxyphenyl)-2-methoxybut-1-yl methyl ether was used as the phenol. There was thus obtained (+)-2-[5-fluoro-3-(7-fluoronaphth-2-ylmethoxy)phenyl]-2-methoxybut-1-yl methyl ether in 89% yield, as an oil, [α]$^{20}$ +17.0° (chloroform, c=1 g/100 ml).

The (+)- and (−)-2-(5-fluoro-3-hydroxyphenyl)-2-methoxybut-1-ylmethyl ethers used as the starting materials for Examples 23 and 24 respectively, were obtained as follows:

A mixture of 2-oxobutyric acid (21 g), sec-butanol (32 ml) and p-toluenesulphonic acid (5.25 g) was stirred at ambient temperature for 75 hours. The mixture was partitioned between diethyl ether and water. The organic phase was dried (MgSO$_4$) and evaporated. There was thus obtained sec-butyl 2-oxobutyrate (16.1 g, 50%).

The product so obtained (15 g) was added dropwise to a solution of 3-benzyloxy-5-fluorophenylmagnesium bromide [prepared by heating a mixture of benzyl 3-bromo-5-fluorophenyl ether (31 g), magnesium powder (2.46 g) and diethyl ether (150 ml) to reflux for 1 hour] in diethyl ether and the mixture was stirred at ambient temperature for 15 hours. The mixture was partitioned between diethyl ether and a saturated aqueous ammonium chloride solution. The organic layer was washed with water, dried (MgSO$_4$) and evaporated. The residue was purified by column chromatography using a 3:1 v/v mixture of methylene chloride and petroleum ether as eluent. There was thus obtained sec-butyl 2-(3-benzyloxy-5-fluorophenyl)-2-hydroxybutyrate (16.3 g, 42%), as an oil.

A mixture of a portion (10 g) of the product so obtained, potassium carbonate (5.4 g), water (5 ml) and methanol (42 ml) was heated to 80° C. for 4 hours. The mixture was evaporated and the residue was partitioned between diethyl ether and water. The aqueous phase was acidified by the addition of concentrated hydrochloric acid and extracted with ethyl acetate. The organic layer was dried (MgSO$_4$) and evaporated. There was thus obtained 2-(3-benzyloxy-5-fluorophenyl)-2-hydroxybutyric acid (7.1 g, 84%), m.p. 105°-106° C.

A mixture of a portion (8.5 g) of the acid so obtained, quinine (9.07 g) and ethanol (100 ml) was stirred at ambient temperature for 30 minutes. The mixture was evaporated to leave the salt as a white solid. This material was dissolved in hot ethanol (28 ml), diisopropyl ether (230 ml) was added and the solution was allowed to stand at ambient temperature for 75 hours. The precipitated solid (7.13 g) was filtered off, dissolved in hot ethanol (35 ml) and then diisopropyl ether (300 ml) was added. The solution was allowed to stand at ambient temperature for 15 hours. The precipitate (4.93 g) was filtered off. The salt so obtained was dissolved in 2N aqueous hydrochloric acid solution and the solution was extracted with diethyl ether. The organic phase was washed with a saturated aqueous sodium chloride solution, dried (MgSO$_4$) and evaporated. There was thus obtained (−)-2-(3-benzyloxy-5-fluorophenyl)-2-hydroxybutyric acid (2.24 g).

The mother liquors from the crystallisation steps described immediately above were combined and evaporated to give the crude quinine salt (13.5 g). This salt was dissolved in 2N aqueous hydrochloric acid solution and extracted with diethyl ether. The organic phase was dried (MgSO$_4$) and evaporated. There was thus obtained crude (−)-2-(3-benzyloxy-5-fluorophenyl)-2-hydroxybutyric acid (5.34 g). This acid was dissolved in diisopropyl ether (320 ml) and (−)-phenethylamine (2.13 g) was added. The solution was stored at ambient temperature for 75 hours. The precipitate (5.8 g) was filtered off. This salt was recrystallised from a mixture of ethanol (20 ml) and diisopropyl ether (500 ml). The precipitate (2.71 g) was filtered off, dissolved in 2N aqueous hydrochloric acid solution and extracted with diethyl ether. The organic phase was washed with a saturated aqueous sodium chloride solution, dried (MgSO$_4$) and evaporated to give (+)-2-(3-benzyloxy-5-fluorophenyl)-2-hydroxybutyric acid (1.86 g).

A solution of diazomethane in diethyl ether was added to a solution of (−)-2-(3-benzyloxy-5-fluorophenyl)-2-hydroxybutyric acid (2.24 g) in diethyl ether (35 ml) until the reaction mixture retained a yellow colouration. The mixture was evaporated to give methyl (−)-2-(3-benzyloxy-5-fluorophenyl)-2-hydroxybutyrate (2.27 g).

Lithium aluminium hydride (0.345 g) was added to a solution of the ester so obtained in diethyl ether (70 ml) and the mixture was stirred at ambient temperature for 1 hour. Water (10 ml) was added dropwise and the mixture was filtered. The organic layer was dried (MgSO$_4$) and evaporated to give (−)-2-(3-benzyloxy-5-fluorophenyl)butane-1,2-diol (2.2 g), as an oil.

Using the procedure described in Example 1, a portion (0.29 g) of the diol so obtained was reacted with methyl iodide to give (−)-2-(3-benzyloxy-5-fluorophenyl)-2-methoxybut-1-yl methyl ether in 99% yield, as an oil.

Using the procedure described in the last paragraph of Note a. below Table IV in Example 13, the product so obtained was hydrogenolysed to give (−)-2-(5-fluoro-3-hydroxyphenyl)-2-methoxybut-1-yl methyl ether (0.22 g, 96%), as an oil.

Using the procedure described in the four paragraphs immediately above, (+)-2-(3-benzyloxy-5-fluorophenyl)-2-hydroxybutyric acid was converted into (+)-2-(5-fluoro-3-hydroxyphenyl)-2-methoxybut-1-yl methyl ether in 90% yield, as an oil.

EXAMPLE 24

The reaction described in Example 21 was repeated except that (−)-2-(5-fluoro-3-hydroxyphenyl)-2-methoxybut-1-yl methyl ether was used as the phenol. There was thus obtained (−)-2-[5-fluoro-3-(7-fluoronaphth-2-ylmethoxy)phenyl]-2-methoxybut-1-yl methyl ether in 44% yield, as an oil, [α]$^{20}$ −14.1° (chloroform, c=1 g/100 ml).

EXAMPLE 25

The following illustrate representative pharmaceutical dosage forms containing the compound of formula I, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph. Eur | 488.5 |
| Magnesium Stearate | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |

| | |
|---|---|
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE $$Ar^1-A^1-O-Ar^2-\underset{R^3}{\overset{OR^1}{C}}-R^2 \qquad I$$

$$HO-Ar^2-\underset{R^3}{\overset{OR^1}{C}}-R^2 \qquad II$$

$$R^4-O-Ar^2-\underset{R^3}{\overset{OR^1}{C}}-R^2 \qquad III$$

$$R^4-O-Ar^2-\underset{R^3}{\overset{OH}{C}}-R^2 \qquad IV$$

$$Ar^1-A^1-O-Ar^2-\underset{R^3}{\overset{OH}{C}}-R^2 \qquad V$$

What we claim is:

1. A compound of the formula I $$Ar^1-A^1-O-Ar^2-\underset{R^3}{\overset{OR^1}{C}}-R^2 \qquad I$$

wherein $Ar^1$ is phenyl or naphthyl which may optionally bear one or more substituents selected from halogeno, hydroxy, (1–4C)alkyl, (2–4C)alkenyl, (2–4C)alkynyl, (1–4C)alkoxy, hydroxy-(1–4C)alkyl and fluoro-(1–4C)alkyl;

wherein $A^1$ is (1–6C)alkylene, (3–6C)alkenylene, (3–6C)alkynylene or cyclo(3–6C)alkylene;

wherein $Ar^2$ is phenylene which may optionally bear one or two substituents selected from halogeno, hydroxy, nitro, (1–4C)alkyl, (1–4C)alkoxy and fluoro-(1–4C)alkyl;

wherein R$^1$ is (1-6C)alkyl, (3-6C)alkenyl or (3-6C)alkynyl; and wherein R$^2$ is (1-6C)alkyl, (2-6C)alkenyl, (2-6C)alkynyl, fluoro-(1-4C)alkyl, hydroxy-(1-4C)alkyl or (1-4C)alkoxy-(1-4C)alkyl;

wherein R$^3$ is hydroxy-(1-4C)alkyl, (1-4C)alkoxy-(1-4C)alkyl, (3-4C)alkenyloxy-(1-4C)alkyl, (3-4C)alkynyloxy-(1-4C)alkyl or (1-4C)alkoxy-(2-4C)alkoxy-(1-4C)alkyl;

or a pharmaceutically-acceptable salt thereof.

2. A compound of the formula I as claimed in claim 1 wherein

Ar$^1$ is phenyl, naphth-1-yl or naphth-2-yl which may optionally bear one, two or three substituents selected from fluoro, chloro, bromo, iodo, methyl, methoxy, difluoromethyl and trifluoromethyl;

A$^1$ is methylene, ethylene, trimethylene, 1-propenylene, 2-methylprop-1-enylene or 1-propynylene;

Ar$^2$ is 1,3-phenylene or 1,4-phenylene which may optionally bear one substituent selected from chloro, bromo, hydroxy, nitro, methyl, methoxy, and trifluoromethyl;

R$^1$ is methyl, ethyl, allyl or 2-propynyl;

R$^2$ is methyl, ethyl, propyl, vinyl, ethynyl, 1-propynyl, trifluoromethyl, hydroxymethyl or methoxymethyl; and R$^3$ is hydroxymethyl, 1-hydroxyethyl, 2-hydroxyethyl, methoxymethyl, 1-methoxyethyl, 2-methoxyethyl or ethoxymethyl;

or a pharmaceutically-acceptable salt thereof.

3. A compound of the formula I as claimed in claim 1 wherein

Ar$^1$ is phenyl or naphth-2-yl which may optionally bear one or two substituents selected from fluoro, chloro, bromo, methyl, tert-butyl and trifluoromethyl;

A$^1$ is methylene, 1-propenylene or 1-propynylene;

Ar$^2$ is 1,3-phenylene or 1,4-phenylene which may optionally bear one substituent selected from fluoro, chloro, methoxy and trifluoromethyl;

R$^1$ is methyl, ethyl or allyl;

R$^2$ is methyl, ethyl, hydroxymethyl or methoxymethyl; and

R$^3$ is hydroxymethyl, 1-hydroxyethyl, 2-hydroxyethyl, methoxymethyl, 1-methoxyethyl, 2-methoxyethyl, ethoxymethyl, allyloxymethyl, 2-propynyloxymethyl, 1-(2-propynyloxy)ethyl or 2-methoxyethoxymethyl;

or a pharmaceutically-acceptable salt thereof.

4. A compound of the formula I as claimed in claim 1 wherein

Ar$^1$ is phenyl or naphth-2-yl which may optionally bear one substituent selected from fluoro, methyl and trifluoromethyl;

A$^1$ is methylene, 1-propenylene or 1-propynylene;

Ar$^2$ is 1,3-phenylene or 1,4-phenylene which may optionally bear one substituent selected from fluoro, methoxy and trifluoromethyl;

R$^1$ is methyl or ethyl;

R$^2$ is methyl, ethyl, hydroxymethyl or methoxymethyl; and

R$^3$ is 1-hydroxyethyl, 2-hydroxyethyl, methoxymethyl, 1-methoxyethyl, 2-methoxyethyl, ethoxymethyl, 2-propynyloxymethyl or 1-(2-propynyloxy)ethyl;

or a pharmaceutically-acceptable salt thereof.

5. A compound of the formula I as claimed in claim 1 wherein

Ar$^1$ is naphth-2-yl or 7-fluoronaphth-2-yl;

A$^1$ is methylene;

Ar$^2$ is 1,3-phenylene or 5-fluoro-1,3-phenylene;

R$^1$ is methyl;

R$^2$ is methyl, ethyl or methoxymethyl; and

R$^3$ is methoxymethyl, 1-methoxyethyl or 2-propynyloxymethyl;

or a pharmaceutically-acceptable salt thereof.

6. A compound of the formula I as claimed in claim 1 wherein

Ar$^1$ is phenyl;

A$^1$ is 1-propynylene;

Ar$^2$ is 1,3-phenylene or 5-fluoro-1,3-phenylene;

R$^1$ is methyl;

R$^2$ is methyl or ethyl; and

R$^3$ is methoxymethyl;

or pharmaceutically-acceptable salts thereof.

7. A compound of the formula I, or a pharmaceutically-acceptable salt thereof, as claimed in claim 1 selected from the group consisting of 2-methoxy-2-[3-(naphth-2-ylmethoxy)phenyl]but-1-yl methyl ether, 2-methoxy-2-[3-(naphth-2-ylmethoxy)phenyl]prop-1-yl methyl ether, 2-methoxy-2-[3-(naphth-2-ylmethoxy)phenyl]but-1-yl 2-propynyl ether, 2-[5-fluoro-3-(7-fluoronaphth-2-ylmethoxy)phenyl]-2-methoxybut-1-yl methyl ether and 2-methoxy-2-[5-fluoro-3-(3-phenylprop-2-ynyloxy)phenyl]but-1-yl methyl ether.

8. A pharmaceutical composition suitable for use in producing inhibition of 5-lipoxygenase which comprises an effective amount of a compound of the formula I, or a pharmaceutically acceptable salt thereof, as claimed in any one of claims 1 to 7 in association with a pharmaceutically-acceptable diluent or carrier.

9. A method of treating a disease or medical condition mediated alone or in part by one or more leukotrienes which comprises administering to a warm-blooded animal requiring such treatment an effective amount of a compound of the formula I, or a pharmaceutically-acceptable salt thereof, as claimed in any one of claims 1 to 7.

* * * * *